US011039932B2

(12) United States Patent
Brown et al.

(10) Patent No.: US 11,039,932 B2
(45) Date of Patent: Jun. 22, 2021

(54) SPINAL IMPLANTS AND RELATED INSTRUMENTS AND METHODS

(71) Applicant: CTL Medical Corporation, Addison, TX (US)

(72) Inventors: Stephen P. Brown, South Jordan, UT (US); Jared M. White, Draper, UT (US); Chad Wayne Lewis, Erie, CO (US)

(73) Assignee: CTL Medical Corporation, Addison, TX (US)

( * ) Notice: Subject to any disclaimer, the term of this patent is extended or adjusted under 35 U.S.C. 154(b) by 0 days.

(21) Appl. No.: 16/153,511

(22) Filed: Oct. 5, 2018

(65) Prior Publication Data

US 2019/0038429 A1 Feb. 7, 2019

Related U.S. Application Data

(63) Continuation of application No. 15/389,346, filed on Dec. 22, 2016, now Pat. No. 10,092,414, which is a continuation of application No. 14/500,671, filed on Sep. 29, 2014, now Pat. No. 9,526,629.

(60) Provisional application No. 61/883,687, filed on Sep. 27, 2013.

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4611* (2013.01); *A61F 2002/3082* (2013.01); *A61F 2002/30112* (2013.01); *A61F 2002/30784* (2013.01); *A61F 2002/30904* (2013.01); *A61F 2002/4627* (2013.01); *A61F 2002/4629* (2013.01)

(58) Field of Classification Search
CPC .................. A61F 2/44–447; A61F 2/46–4684
See application file for complete search history.

(56) References Cited

U.S. PATENT DOCUMENTS

| 2007/0270966 A1* | 11/2007 | Chen ...................... A61B 50/22 623/17.11 |
| 2008/0140085 A1* | 6/2008 | Gately .................. A61F 2/4465 606/99 |
| 2010/0168798 A1* | 7/2010 | Clineff .................. A61F 2/4611 606/279 |
| 2010/0211119 A1* | 8/2010 | Refai .................... A61F 2/4611 606/86 A |
| 2010/0256760 A1* | 10/2010 | Hansell ................. A61F 2/4611 623/17.11 |
| 2010/0298941 A1* | 11/2010 | Hes ....................... A61F 2/4425 623/17.16 |

(Continued)

*Primary Examiner* — Nicholas J Plionis
(74) *Attorney, Agent, or Firm* — Brianspark Associates, LLC

(57) ABSTRACT

Apparatus and systems relating to spinal implants and instruments for installing such implants. In some embodiments, the system may comprise a spinal implant, an inserter, an intermediary piece, and/or an installation rod. The spinal implant may comprise an at least partially threaded opening configured to receive the installation rod. The opening may be positioned within a fixed wall of the spinal implant, and the opening may comprise a peripheral edge defined by the wall of the spinal implant.

7 Claims, 24 Drawing Sheets

(56) References Cited

U.S. PATENT DOCUMENTS

| | | | |
|---|---|---|---|
| 2011/0190892 A1* | 8/2011 | Kirschman | A61F 2/447 623/17.16 |
| 2012/0165943 A1* | 6/2012 | Mangione | A61F 2/4465 623/17.16 |
| 2013/0023937 A1* | 1/2013 | Biedermann | A61F 2/4465 606/279 |
| 2013/0053901 A1* | 2/2013 | Cormier | A61B 17/7032 606/305 |
| 2013/0268075 A1* | 10/2013 | McKay | A61F 2/447 623/17.16 |
| 2014/0172107 A1* | 6/2014 | Thirugnanasambandam | A61F 2/4611 623/17.16 |
| 2014/0277483 A1* | 9/2014 | Ullrich, Jr. | A61F 2/28 623/17.16 |

\* cited by examiner

SPINAL IMPLANTS AND RELATED INSTRUMENTS AND METHODS

RELATED APPLICATIONS

This application is a continuation of co-pending U.S. patent application Ser. No. 15/389,346, filed on Dec. 22, 2016, entitled "SPINAL IMPLANTS AND RELATED INSTRUMENTS AND METHODS," which is a continuation of co-pending U.S. patent application Ser. No. 14/500,671, filed on Sep. 29, 2014, and titled "SPINAL IMPLANTS AND RELATED INSTRUMENTS AND METHODS," which claims the benefit under 35 U.S.C. § 119(e) of U.S. Provisional Patent Application 61/883,687 filed Sep. 27, 2013 and titled "SPINAL IMPLANTS AND RELATED INSTRUMENTS AND METHODS." The aforementioned applications are all hereby incorporated by reference herein in their entireties.

SUMMARY

Disclosed herein are embodiments of systems, apparatus, and methods that relate to spinal implants and instruments for installing such implants. In some embodiments, the implants and related instrumentation may be configured to reduce or eliminate the forces applied to relatively weak portions of the implant, with may be at the peripheral edge(s)/end(s) of an opening/hole in the implant for receiving an instrument, such as a rod. Thus, some embodiments may be configured such that the highest forces applied to an engagement region in the implant, such as threads in the spinal implant, will be applied to the strongest area and/or threads of the implant. This may substantially reduce fractures or other damage that may otherwise be prone to occur, particularly with respect to certain ceramic spinal implants.

In a more particular example of a spinal implant system, the system may comprise a spinal implant comprising a first sidewall, a second sidewall opposite from the first sidewall, an upper surface configured for engaging a first vertebra, and a lower surface configured for engaging a second vertebra adjacent to the first vertebra. The spinal implant may further comprise a first end wall joining the first sidewall and the second sidewall at a first end of the spinal implant, and a second end wall joining the first sidewall and the second sidewall at a second end of the spinal implant opposite from the first end. The second end wall may define a second end wall surface.

At least one of a recess and a protrusion may be formed in the second end wall, and an opening may be positioned within the second end wall. In some embodiments, a v-shaped recess may be provided. In some embodiments, the recess/protrusion may be spaced apart from the opposing sidewalls such that it only extends partially across a rear surface of the implant. Alternatively, the recess/protrusion may extend all of the way across an end of the implant so as to extend from one sidewall to the opposite sidewall. The opening may comprise a threaded region, and wherein the threaded region is spaced apart from the second end wall surface.

The system may further comprise an installation rod configured to be positioned within the opening. The installation rod may comprise a threaded section configured to engage the threaded region of the opening at a location spaced apart from the second end wall surface.

Some embodiments may further comprise an inserter comprising an opening configured to receive the installation rod therethrough. Some embodiments may further comprise an intermediary piece configured to be coupled with the spinal implant and the inserter in between the spinal implant and the inserter. The intermediary piece may comprise at least one of a recess and a protrusion configured to engage the at least one of a recess and a protrusion formed in the second end wall of the spinal implant.

In some embodiments, the spinal implant may further comprise an expanded region within the opening. The expanded region may be configured to accommodate an engagement feature of the installation rod, such as threads. Thus, the expanded region may comprise a diameter greater than a diameter of at least a portion of the opening adjacent to the expanded region, and may be configured to provide clearance for threads on the threaded section of the installation rod. In some embodiments, the expanded region may be defined by a frustoconical shape that tapers so as to expand the diameter of the opening towards a proximal end of the opening.

The installation rod may also, or alternatively, be configured to allow for coupling between the implant and the rod and preferred locations in order to reduce the likelihood of breakage. For example, in some embodiments, the rod may comprise one or more reduced diameter sections positioned adjacent to the threaded section. The reduced diameter section(s) may comprise a diameter less than a diameter of the threads of the threaded section of the rod.

A reduced diameter section may be positioned adjacent to and distally of the threaded section, and the reduced diameter section may comprise a diameter less than a minor diameter of the threads of the threaded section. Another reduced diameter section, or an alternative reduced diameter section, may be positioned adjacent to and proximally of the threaded section, in order to facilitate a desired coupling.

In some embodiments, the installation rod may further comprise a knob positioned adjacent to the reduced diameter section. The knob may comprise a diameter greater than the diameter of the reduced diameter section. The opening in the spinal implant may extend all of the way through the second end wall so as to define a passageway, and, in some such embodiments, the knob may be configured such that at least a portion of the knob extends all of the way through the passageway when the installation rod is coupled with the spinal implant. The knob may, in some embodiments, comprise a flexible material such that the knob compresses as the knob extends through the passageway and at least a portion of the knob expands after extending through the passageway.

The spinal implant may further comprise notches formed in the upper surface and the lower surface of a nose at least partially defined by the first end wall, which may allow the shape of the nose and/or adjacent sidewalls to guide the spinal implant in a desired manner during installation. In some embodiments, the spinal implant may further comprise a pair of fins positioned along a peripheral edge of at least one of the first and second sidewalls, which may further, or as an alternative, provide such desired guidance during installation. The fins may comprise partial fins that extend only along a peripheral edge of a nose of the spinal implant at least partially defined by the first end wall. Alternatively, the fins may extend all of the way, or at least substantially the entire way, along one or both sidewalls of the implant.

In another particular example of a spinal implant system, the system may comprise a spinal implant comprising an opening configured to receive an installation rod for installing the spinal implant within an intervertebral space of a patient. The opening may be positioned within a wall of the spinal implant, and the opening may comprise a peripheral edge defined by the wall of the spinal implant.

The system may further comprise an installation rod configured to be positioned within the opening. The installation rod may comprise an engagement section configured to engage a portion of the spinal implant defining the opening at a location spaced apart from the peripheral edge such that the highest forces applied to the spinal implant in coupling the spinal implant with the installation rod during installation of the spinal implant are not applied to the portion of the opening defined by the peripheral edge.

In some embodiments, the opening may be at least partially threaded, and the installation rod may comprise a threaded section configured to engage the opening at a location spaced apart from the peripheral edge.

In some embodiments, the spinal implant may further comprise an expanded region within the opening. The expanded region may comprise a diameter greater than a diameter of at least a portion of the opening adjacent to the expanded region, and may be configured to provide clearance for threads on the threaded section of the installation rod.

The installation rod may comprise a first unthreaded section positioned adjacent to and distally of the threaded section and/or a second unthreaded section positioned adjacent to and proximally of the threaded section. The first unthreaded section and the second unthreaded section may both comprise a diameter less than a major diameter of the threads of the threaded section. In some embodiments, one or both of the unthreaded sections may comprise a diameter less than a minor diameter of the threads of the threaded section.

In another particular example of a spinal implant system, the system may comprise a spinal implant comprising a first sidewall, a second sidewall opposite from the first sidewall, an upper surface configured for engaging a first vertebra, and a lower surface configured for engaging a second vertebra adjacent to the first vertebra. At least one opening may extend between the upper surface and the lower surface.

A first end wall may join the first sidewall and the second sidewall at a first end of the spinal implant, and a second end wall may join the first sidewall and the second sidewall at a second end of the spinal implant opposite from the first end. The second end wall may define a second end wall surface. At least one of a recess and a protrusion may be formed in the second end wall, and may be configured to engage a corresponding protrusion or recess of a spinal installation instrument.

A hole may be positioned in the at least one of a recess and a protrusion in the second end wall. The hole may extend through the second end wall and into the at least one opening, and may be configured to receive an installation rod for installing the spinal implant within an intervertebral space of a patient. The hole may comprise a threaded region that may be spaced apart from the second end wall surface and/or may be spaced apart from an end of the hole opposite from the second end wall surface. The hole may further comprise an expanded region adjacent to the second end wall surface that may have a diameter greater than a diameter of at least a portion of the hole adjacent to the expanded region, which may allow for accommodating the threads during coupling of the implant and the rod.

The system may further comprise a spinal installation instrument, which may comprise an inserter and an intermediary piece configured to be coupled with the spinal implant and the inserter in between the spinal implant and the inserter, both of which may be configured to receive an installation rod therethrough, such as by way of a contiguous opening through the inserted and intermediary piece. The intermediary piece may comprise at least one of a protrusion and a recess configured to engage the at least one of a recess and a protrusion formed in the second end wall of the spinal implant.

The spinal installation instrument may further comprise an installation rod configured to be positioned within and extend through the inserter and the intermediary piece. The installation rod may comprise a threaded section configured to engage the threaded portion of the spinal implant at a location spaced apart from both opposite ends of the hole. The expanded region of the spinal implant may be configured to provide clearance for threads on the threaded section. The installation rod may further comprise at least one unthreaded section positioned adjacent to the threaded section, which may have a diameter less than a major diameter of the threads of the threaded section.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
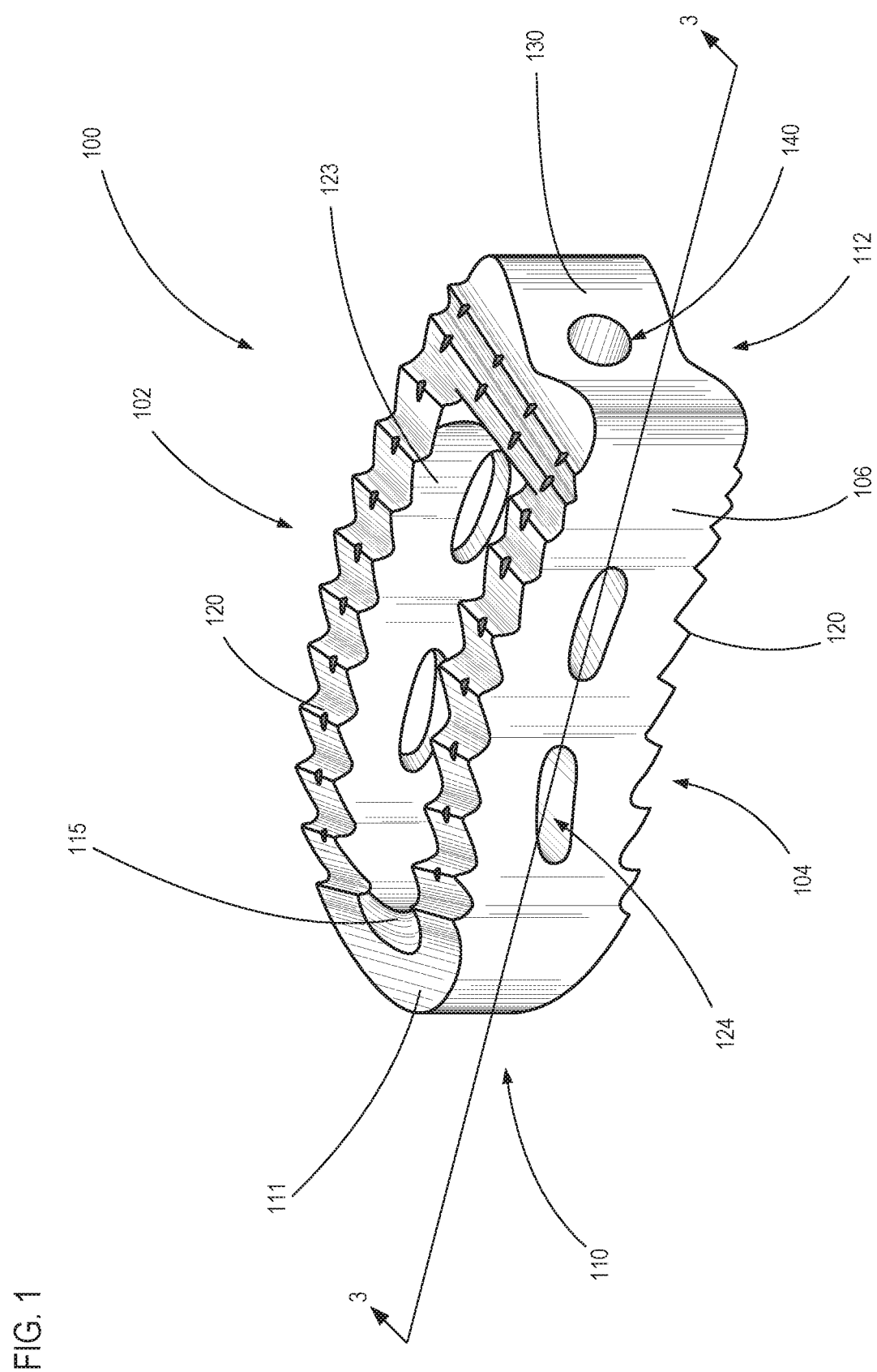
FIG. 1 is a perspective view of a spinal implant according to one embodiment.

A detailed description of apparatus, systems, and methods consistent with various embodiments of the present disclosure is provided below. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In addition, while numerous specific details are set forth in the following description in order to provide a thorough understanding of the embodiments disclosed herein, some embodiments can be practiced without some or all of these details. Moreover, for the purpose of clarity, certain technical materials, structures, or operations that are known in the related art have not been shown or described in detail in order to avoid unnecessarily obscuring the disclosure.

Various embodiments of apparatus, methods, and systems are disclosed herein that relate to spinal implants and instruments for installing such implants. For example, some embodiments may comprise intervertebral spinal spacers. Some embodiments may comprise instruments for installing such intervertebral spinal implants and/or intermediary pieces configured for being positioned between an inserter and a spinal implant.

Some embodiments may be particularly useful for spinal implants comprising a ceramic material, such as a silicon nitride ceramic material. Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide, and strontium oxide, can be processed to form a doped composition of silicon nitride. In some embodiments, powders of silicon nitride may be used to form the ceramic implants, either alone or in combination with one or more of the dopants referenced above. Other examples of suitable silicon nitride materials are described in U.S. Pat. No. 7,666,229 titled "Ceramic-Ceramic Articulation Surface Implants," which is also hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference, However, it should be understood that many of the inventive concepts and principles disclosed herein can be applied to implants comprising any materials known or hereafter developed, including, for example, titanium, titanium alloys, steel, polymers, poly-ether-ether-ketone (PEEK), bone graft, biological compounds, other ceramics/composites, and the like.

Additional details regarding certain preferred embodiments will now be described in greater detail with reference to the accompanying drawings. FIG. 1 depicts a perspective view of an embodiment of a spinal implant 100. Spinal implant 100 comprises an upper surface 102, a lower surface 104, a first side wall surface 106, a second side wall surface 108 opposite from surface 106, a front end wall surface 110 comprising a nose 111, and a rear end wall surface 112 opposite from front end wall surface 110 comprising a recess 130. Recess 130 comprises a v shape that may be configured to directly interface with a spinal installation instrument or to indirectly couple with an intermediary piece configured to directly interface with such an instrument.

Upper and lower surfaces 102 and 104 may both comprise a plurality of engagement structures 120, which in the depicted embodiment comprise rows of teeth. Teeth 120 are arranged in rows and radiate from a focal point positioned along the axis of spinal implant 100. Spinal implant 100 and its axis extend along an arcuate path to form a shape substantially in the form of a kidney. More particularly, first side wall surface 106 is concave and second side wall surface 108 is convex to form the kidney-like shape.

Each of the rows in which teeth 120 are arranged is at least substantially perpendicular to both the first side wall surface 106 and the second side wall surface 108. In addition, in the depicted embodiment, the spacing between the rows of teeth decreases from the front end wall surface 110 or nose 111 to the rear end wall surface 112.

Figure 2:
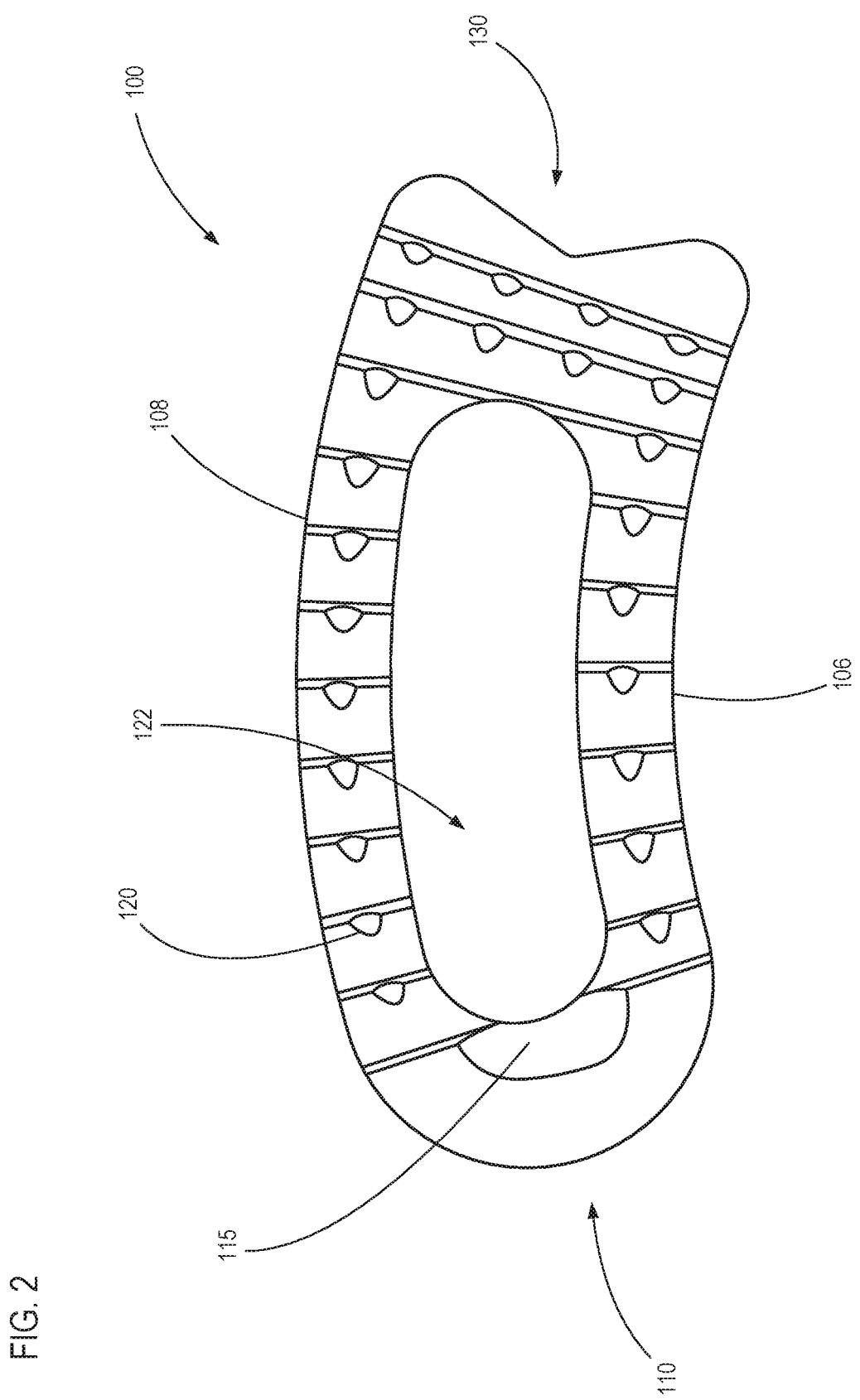
FIG. 2 is a top plan view of the spinal implant of FIG. 1.

Upper surface 102 also comprises an opening 122, as shown in FIG. 2. As best shown in the upper plan view of FIG. 2, opening 122 also extends through lower surface 104 to allow for ingrowth of bony material therethrough. Portions of the inner surface of opening 122, along with side wall surfaces 106 and 108, form walls or rails 123 that extend along the periphery of spinal implant 100.

Figure 3:
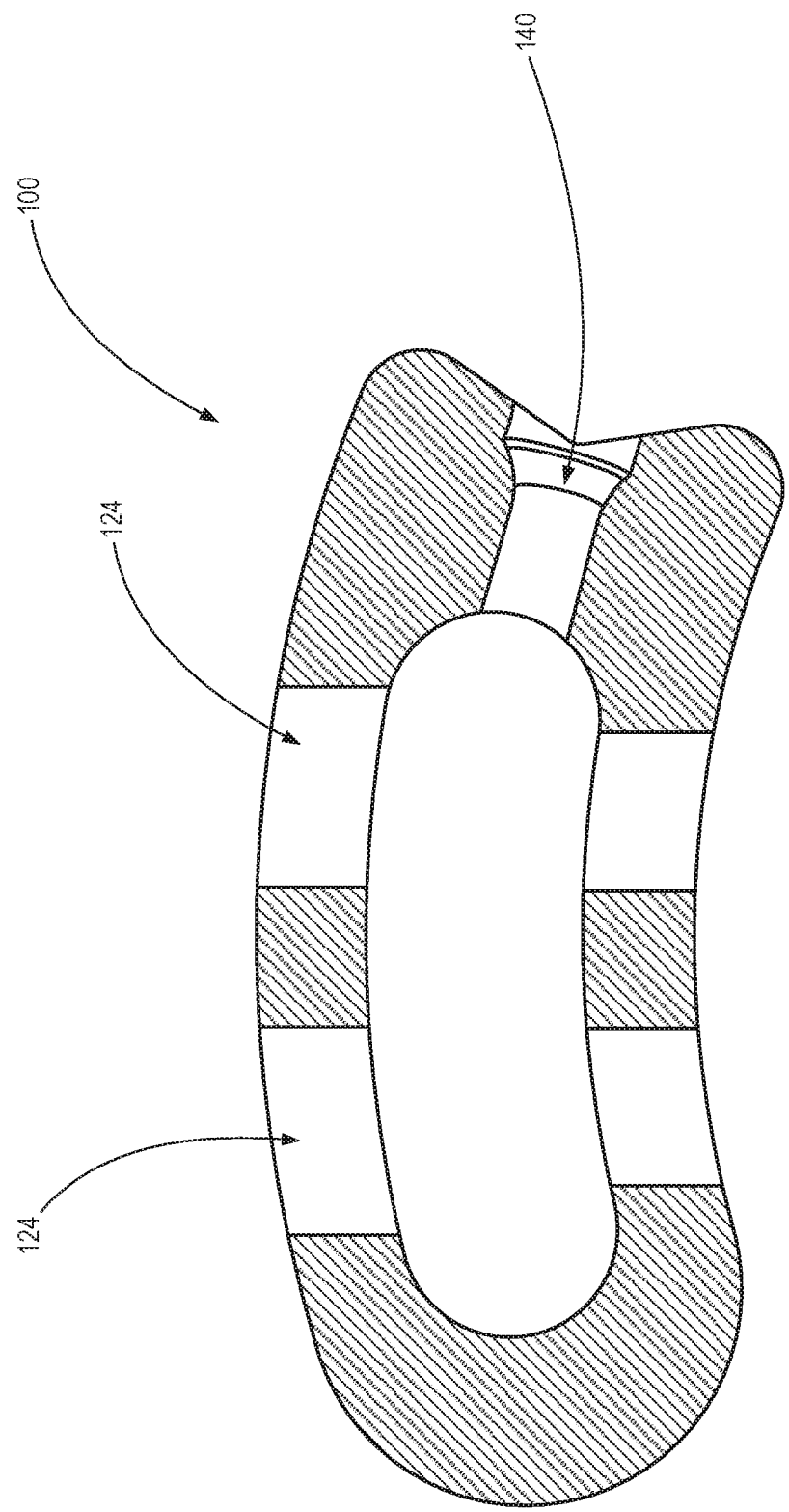
FIG. 3 is a cross-sectional view of the spinal implant of FIGS. 1 and 2.

As illustrated in FIG. 1, and in the cross-sectional view of FIG. 3, openings 124 are also formed in side wall surfaces 106 and 108. Of course, alternative embodiments are contemplated in which differing numbers and/or shapes of side wall, top surface, and/or lower surface openings are formed as desired. For example, in some embodiments that may be designed as lordotic spinal implants, the implant may be sloped from one lateral side to the opposite lateral side. In some such embodiments, it may be useful to provide side wall openings that are larger on the side of the implant having the greatest height (typically the anterior side) and smaller openings in the side of the implant having the smallest height (typically the posterior side).

Rear end wall surface 112 forms a recessed area 130 formed into the shape of a fishtail. Recess 130 may be configured to engage a corresponding surface of an inserter tool, as discussed in greater detail below. Moreover, as also shown in FIG. 1, and in the cross-sectional view of FIG. 3, spinal implant 100 may have an opening 140 formed in recessed area 130 of rear end wall surface 112. In some embodiments, opening 140 may be threaded so as to allow for engagement with an inserter tool. In some embodiments, other retention structures may be used to facilitate engagement between spinal implant 100 and an installation rod or other inserter instrumentation. Although in the depicted embodiment, opening 140 extends all of the way through the rear wall defining rear end wall surface 112, alternative embodiments are contemplated in which opening 140 comprises a blind hole.

In some embodiments, such as the embodiment depicted in FIG. 1, opening 140 may be formed within a central region of recess 130. In the embodiment depicted in FIGS. 1-3, it can also be seen that opening 140 extends along the arcuate axis of spinal implant 100. However, as discussed below in connection with other figures, other embodiments are contemplated in which the inserter opening does not extend along this axis.

Nose 111 tapers as it extends from side wall surfaces 106 and 108 to the tip of the implant. This taper may extend along both the upper surface 102 and the lower surface 104 of the implant such that nose 111 is thinner than the rest of spinal implant 100.

In the depicted embodiment, a notch 115 is also formed in the material defining nose 111 adjacent to opening 122. In some embodiments, notch 115 may comprise a groove. Although not visible in the figures, in preferred embodiments, a corresponding notch may also be formed in the opposite surface of nose 111 (adjacent to lower surface 104) in a similar manner. It has been discovered that one or more such notches may be beneficial in allowing rails/walls 123 to serve as a guide rail to guide spinal implant 100 in a desired path during a surgical procedure to install implant 100 in a patient's intervertebral space. In embodiments lacking such notches 115, the nose 111 may undesirably hinder the ability of rails/walls 123 to guide or curve the implant 100 during installation.

As also shown in the figures (best shown in FIG. 1), in some embodiments notch 115 may be formed directly in one or both of the tapered surfaces (upper and lower) of nose 111. As also shown in the figures, notch 115 extends from the peak of a tooth 120 on one side of implant 100 to a tooth 120 in the same row on the opposite side of implant 100.

Figure 4:
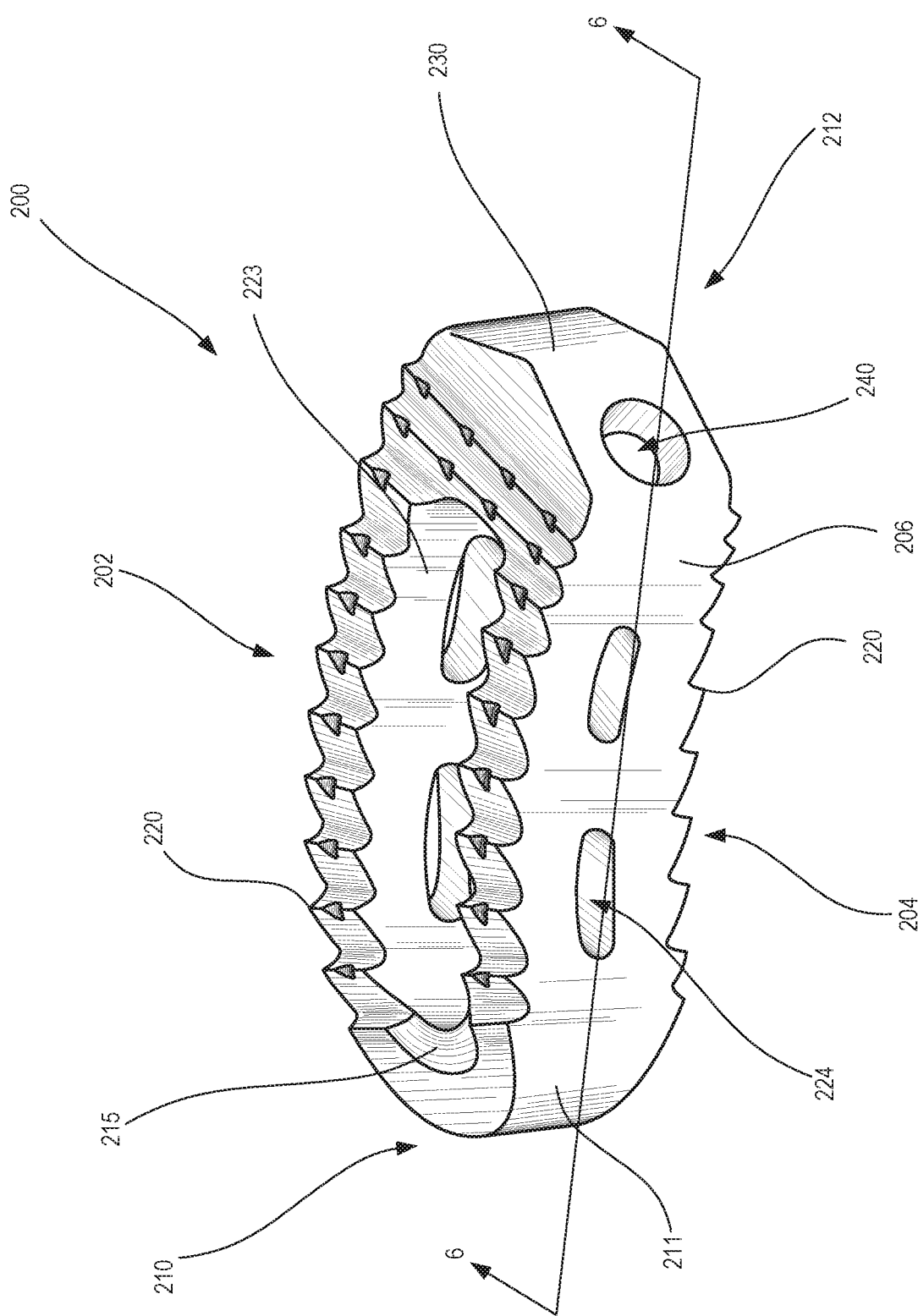
FIG. 4 is a perspective view of a spinal implant according to another embodiment.
Figure 5:
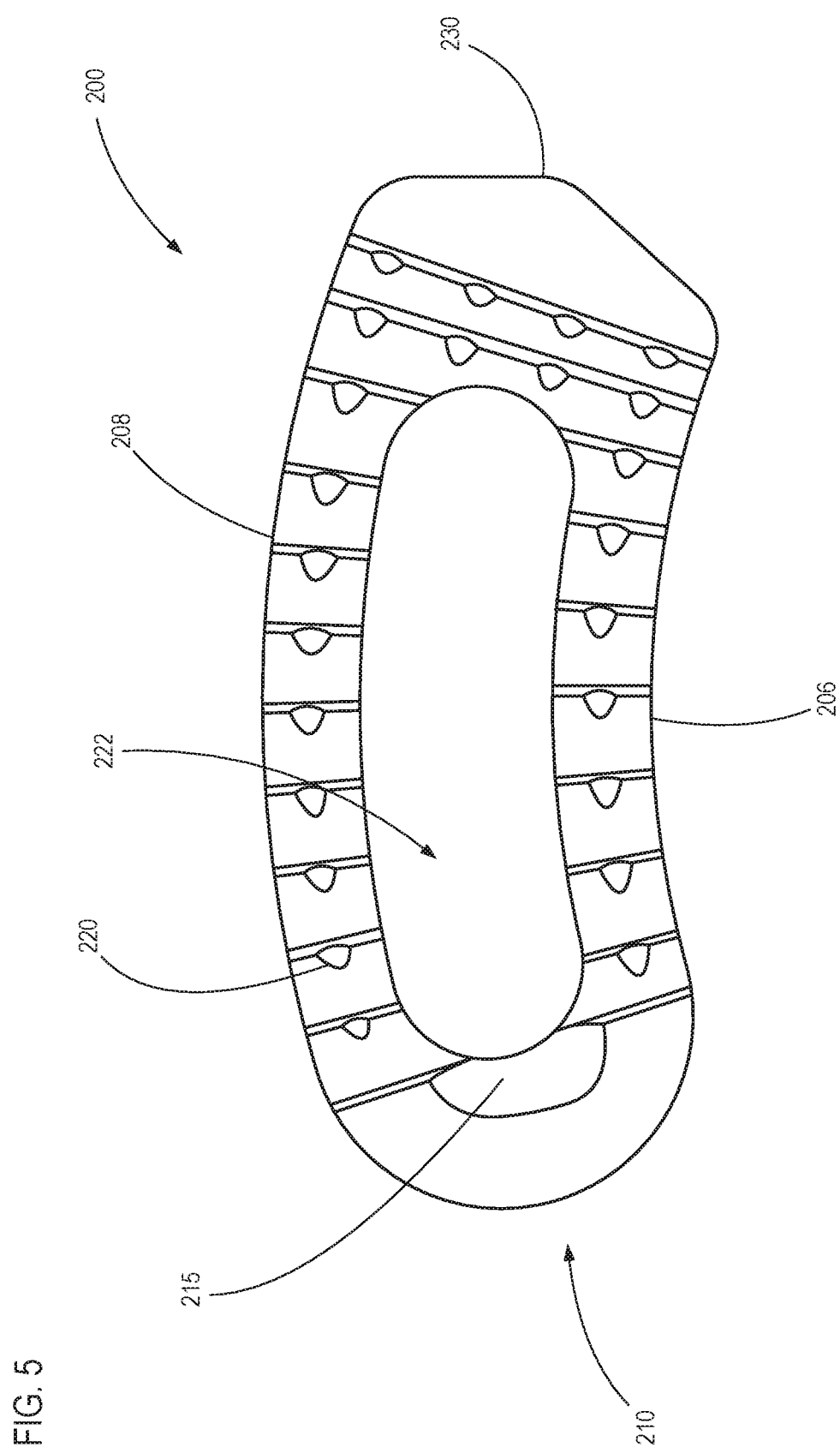
FIG. 5 is a top plan view of the spinal implant of FIG. 4.
Figure 6:
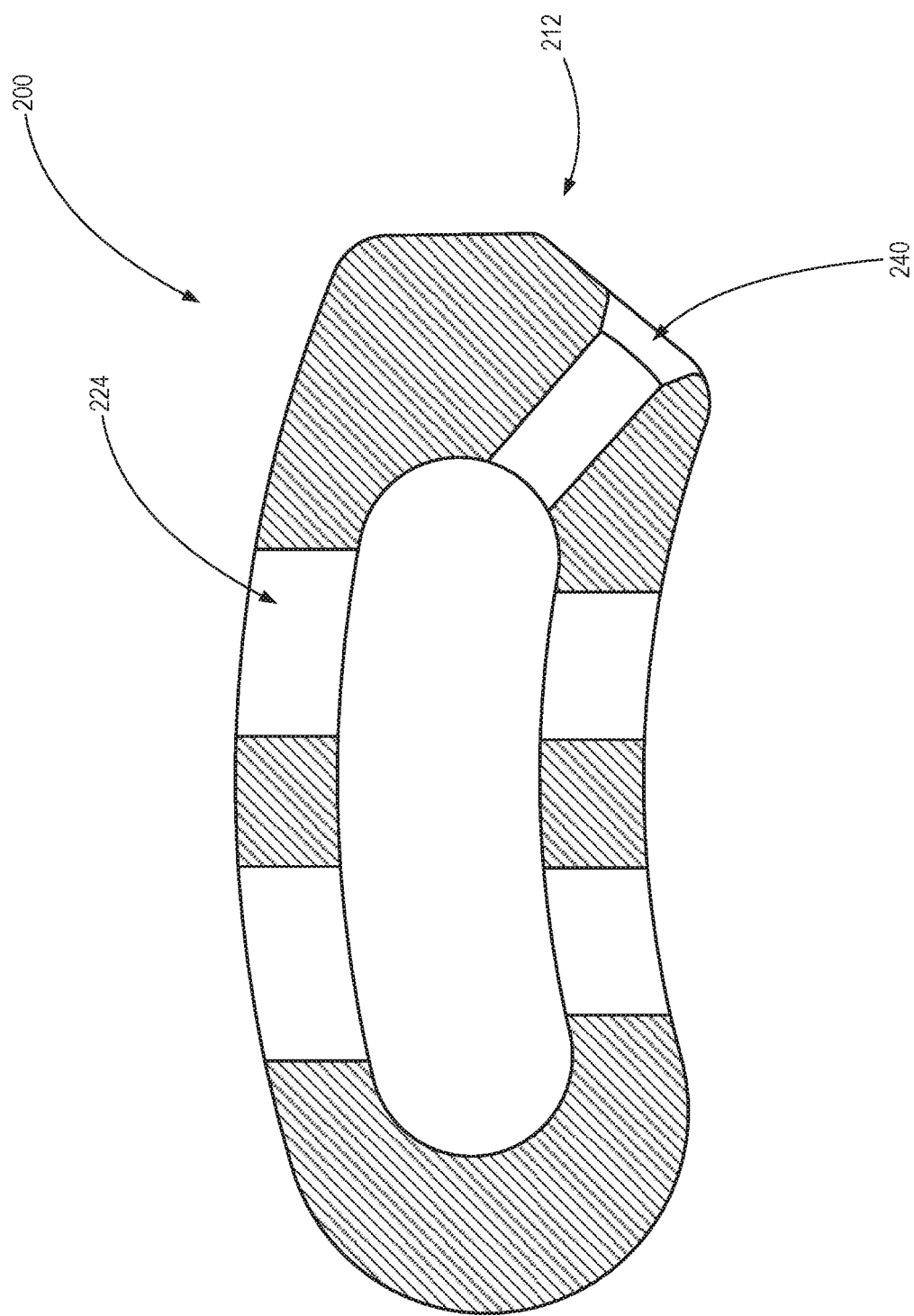
FIG. 6 is a cross-sectional view of the spinal implant of FIGS. 4 and 5.

FIG. 4 is a perspective view of another embodiment of a spinal implant 200 (with other views depicted in FIGS. 5 and 6). Like spinal implant 100, spinal implant 200 comprises an upper surface 202, a lower surface 204, a first side wall surface 206, a second side wall surface 208 opposite from surface 206, a front end wall surface 210 comprising a nose 211, and a rear end wall surface 212 opposite from front end wall surface 210. However, rear end wall surface 212 comprises a protrusion 230 rather than a recess. Protrusion 230 comprises a v shape that protrudes from rear end wall surface 212. Like the v-shaped recess 130 of spinal implant 100, v-shaped protrusion 230 may be configured to directly interface with a spinal installation instrument or to indirectly couple with an intermediary piece configured to directly interface with such an instrument.

Upper and lower surfaces 202 and 204 both comprise a plurality of teeth 220 arranged in rows. Teeth 220 radiate from a focal point positioned along the axis of spinal implant 200. However, in other embodiments comprising such teeth, they may be instead arranged in parallel rows. Spinal implant 200 and its axis extend along an arcuate path to form a kidney shape. Each of the rows in which teeth 220 are arranged is at least substantially perpendicular to both the first side wall surface 206 and the second side wall surface 208. In addition, like the embodiment of FIGS. 1-3, the spacing between the rows of teeth decreases from the front end wall surface 210 and/or nose 211 to the rear end wall surface 212.

Upper surface 202 also comprises an opening 222 that extends through lower surface 204 to allow for ingrowth of bony material therethrough. Portions of the inner surface of opening 222, along with side wall surfaces 206 and 208, form walls or rails 223 that extend along the periphery of spinal implant 200. Openings 224 are also formed in side wall surfaces 206 and 208.

As shown in FIG. 4, spinal implant 200 also comprises an opening 240 formed in one of the two surfaces forming v-shaped protrusion 230. It should be understood, however, that a wide variety of alternative embodiments are contemplated in which alternative shapes/structures are formed on one or both of the end wall surfaces of the implant. For example, some embodiments may comprise a u-shaped protrusion, a u-shaped recession, or any other shape, geometry, and/or feature that serves to prevent or at least inhibit rotation between an inserter and, the implant. Still other embodiments may lack any such shape, geometry, or feature if desired.

In some embodiments, opening 240 may be threaded so as to allow for engagement with an inserter tool. Opening 240 does not extend along the arcuate axis of spinal implant 200. More specifically, opening 240 is positioned at an angle of about 20 degrees with respect to the arcuate axis of spinal implant 200. In some embodiments, the angle at which the opening is formed with respect to the axis of the implant may be between about 10 degrees and about 45 degrees. In some such embodiments, the angle at which the opening is formed with respect to the axis of the implant may be between about 15 degrees and about 30 degrees. The surface of v-shaped protrusion 230 in which opening 240 is formed may therefore also be angled with respect to the axis of implant 200 at this angle. This angling may be useful for certain applications, and for use in connection with certain inserters. For example, angling the inserter hole may be useful for positioning spinal implant 200 at a desired angle during an installation surgery.

It can also be seen that opening 240 is not only formed at an angle with respect to the axis of implant 200, but it also begins at a location offset from (below from the perspective of the cross-sectional view of FIG. 6) this axis.

Like spinal implant 100, spinal implant 200 also comprises a nose 211 that tapers as it extends from side wall surfaces 206 and 208 to the tip of the implant along both the upper surface 202 and the lower surface 204 of the implant. Spinal implant 200 further comprises notches 215 formed in both opposite surfaces of nose 211. As mentioned above, this feature may be useful in allowing the sidewalls/rails 223 of implant 200 to be used to guide implant 200 in a curved path as the implant 200 is installed in a patient's intervertebral space.

Figure 7:
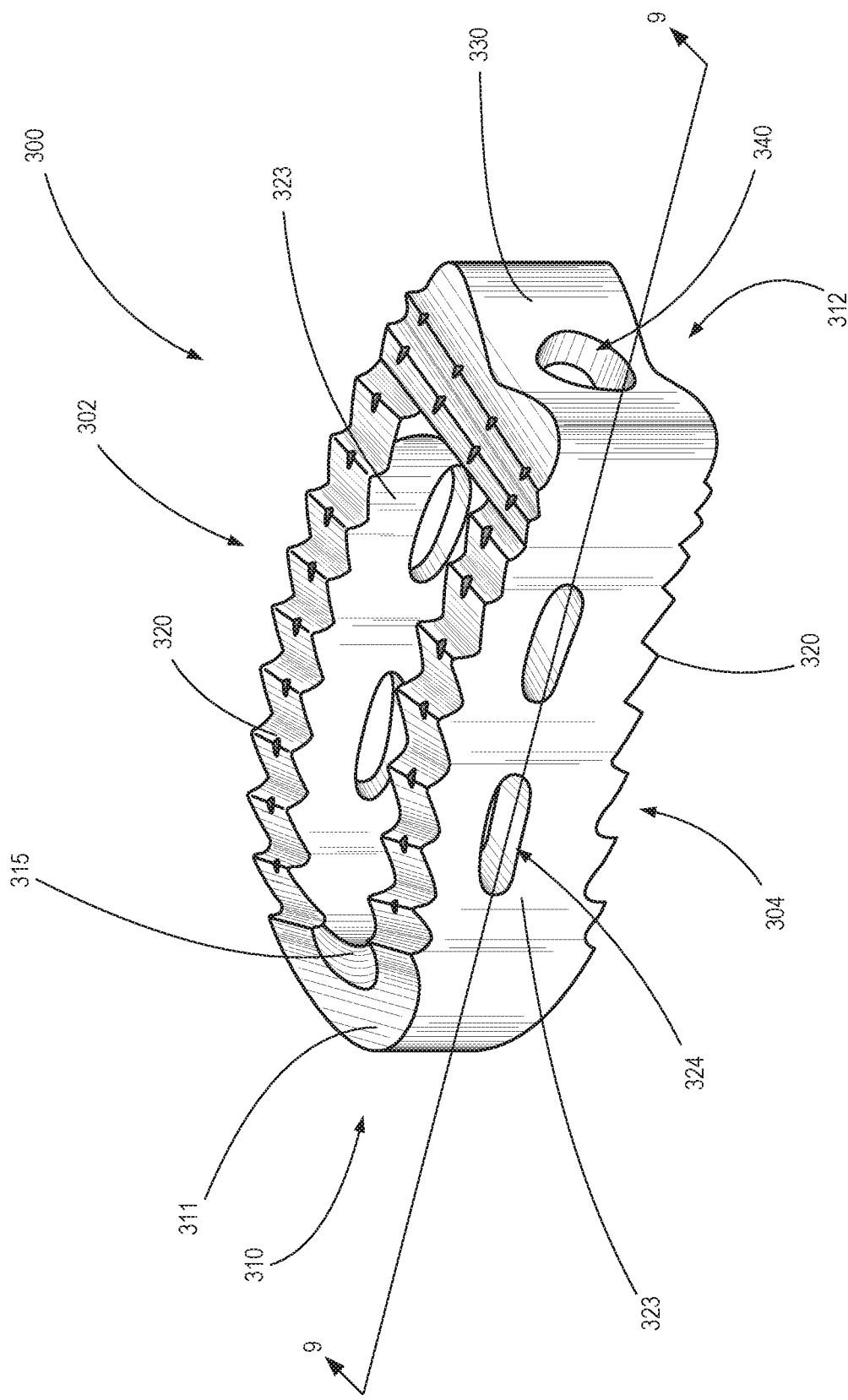
FIG. 7 is a perspective view of a spinal implant according to yet another embodiment.
Figure 8:
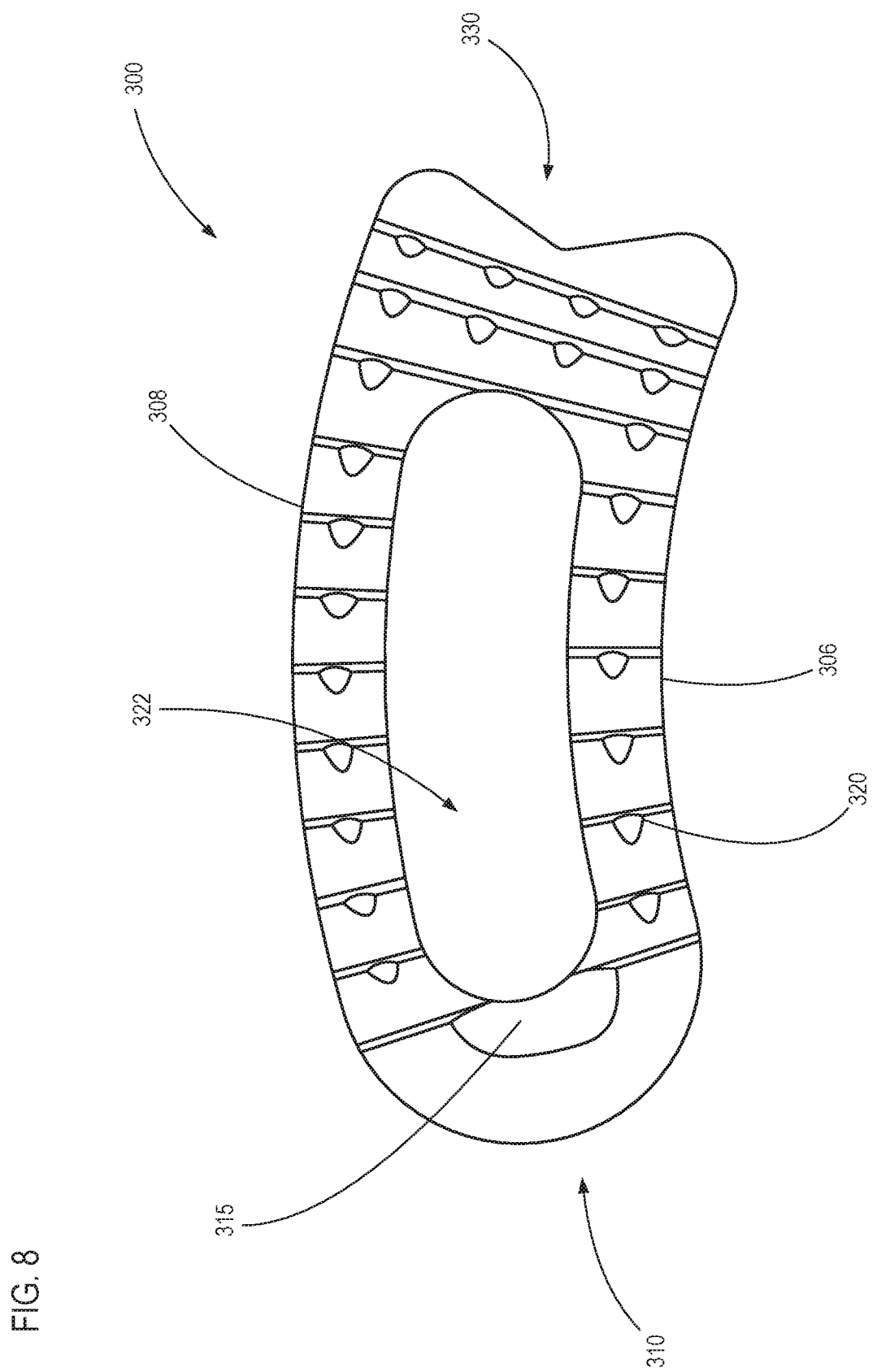
FIG. 8 is a top plan view of the spinal implant of FIG. 7.
Figure 9:
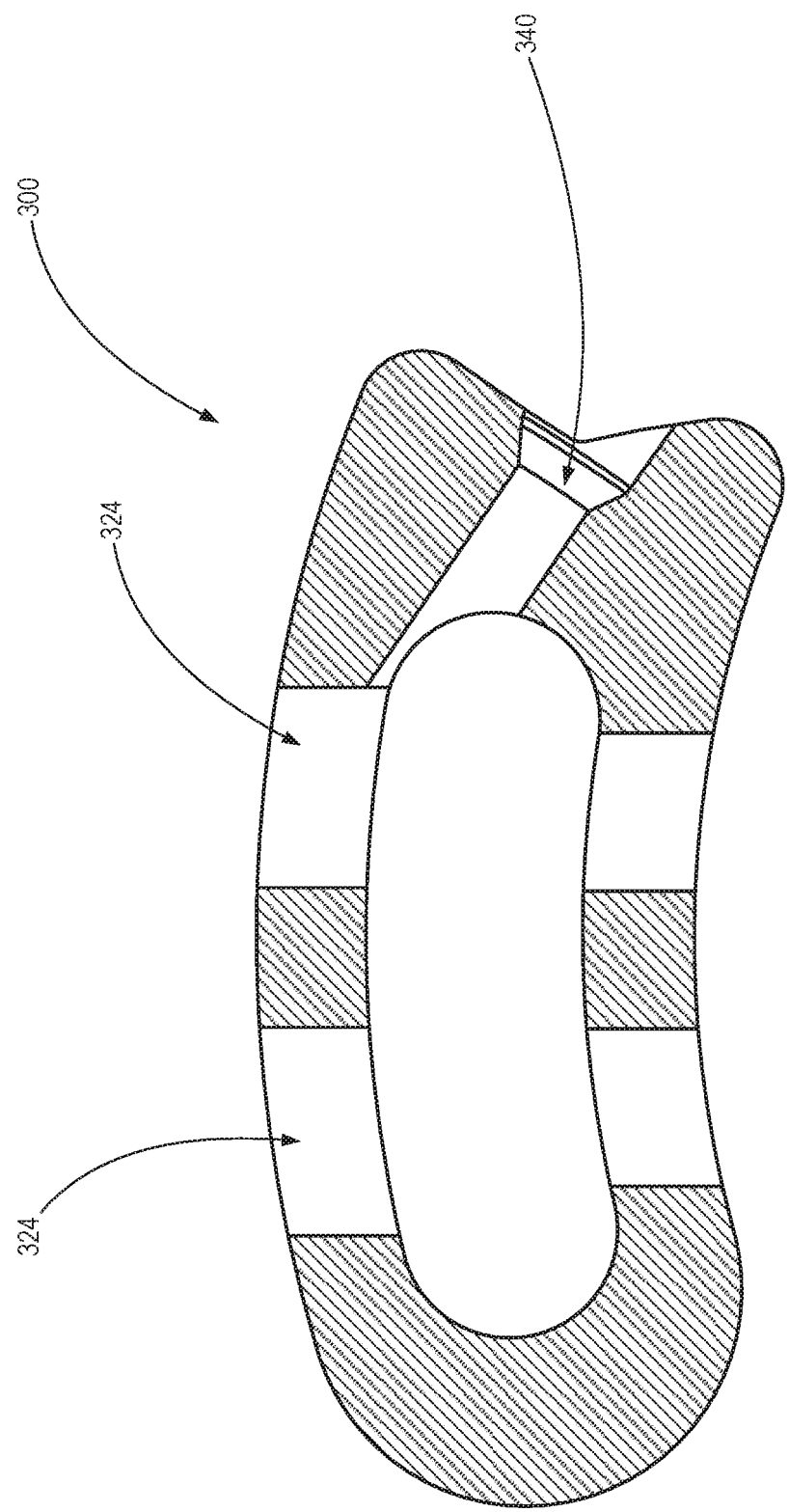
FIG. 9 is a cross-sectional view of the spinal implant of FIGS. 7 and 8.

FIG. 7 is a perspective view of a spinal implant 300 according to yet another embodiment. FIG. 8 is a top plan view of spinal implant 300, and FIG. 9 is a cross-sectional view of spinal implant 300. Like spinal implants 100 and 200, spinal implant 300 comprises an upper surface 302, a lower surface 304, a first side wall surface 306, a second side wall surface 308 opposite from surface 306, a front end wall surface 310 comprising a nose 311, and a rear end wall surface 312 opposite from front end wall surface 310.

Rear end wall surface 312 comprises a recess 330, similar to recess 130 of spinal implant 100. Recess 330 comprises a v shape formed in a fishtail configuration that may be configured to directly interface with a spinal installation instrument or to indirectly couple with an intermediary piece configured to directly interface with such an instrument. Spinal implant 300 also comprises an opening 340 formed in v-shaped recess 330. In some embodiments, opening 340 may be threaded so as to allow for engagement with an inserter tool.

However, unlike spinal implant 100, opening 340 does not extend along the arcuate axis of spinal implant 300. More specifically, opening 340 is positioned at an angle with respect to the arcuate axis of spinal implant 300. In some embodiments, the angle at which the opening is formed with respect to the axis of the implant may be between about 10 degrees and about 45 degrees. In some such embodiments, the angle at which the opening is formed with respect to the axis of the implant may be between about 15 degrees and about 30 degrees. This angling may be useful for certain applications, and for use in connection with certain inserters. For example, angling the inserter hole may be useful for positioning spinal implant 300 at a desired angle during an installation surgery.

It can also be seen in FIG. 9 that, unlike spinal implant 200, although opening 340 extends at an angle with respect to the arcuate angle of spinal implant 300, opening 340 begins at a location coincident with this axis. In other words, opening 340 is formed at a midpoint of recess 330, which is along the arcuate axis of implant 300, but then extends at an angle (upward from the perspective of FIG. 9) from this arcuate axis. It can also be seen from FIG. 9 that opening 340 extends into opening 322. However, alternative embodiments are contemplated in which opening 340 may form a blind hole that is closed at one end and does not extend into opening 322 (or another similar opening) of implant 300.

Like implants 100 and 200, upper and lower surfaces 302 and 304 of implant 300 both comprise a plurality of teeth 320 arranged in rows. Teeth 320 radiate from a focal point positioned along the axis of spinal implant 300. In addition, spinal implant 300 and its axis extend along an arcuate path to form a kidney shape. Each of the rows in which teeth 320 are arranged is at least substantially perpendicular to both the first side wall surface 306 and the second side wall surface 308. In addition, like the embodiments depicted in the previous figures, the spacing between the rows of teeth decreases from the front end wall surface 310 or nose 311 to the rear end wall surface 312.

Upper surface 302 also comprises an opening 322 that extends through lower surface 304 to allow for ingrowth of bony material therethrough. Portions of the inner surface of opening 322, along with side wall surfaces 306 and 308, form walls or rails 323 that extend along the periphery of spinal implant 300. Openings 324 are also formed in side wall surfaces 306 and 308.

Like spinal implants 100 and 200, spinal implant 300 also comprises a nose 311 that tapers as it extends from side wall surfaces 306 and 308 to the tip of the implant along both the upper surface 302 and the lower surface 304 of the implant. Spinal implant 300 further comprises notches 315 formed in both opposite surfaces of nose 311.

Figure 10:
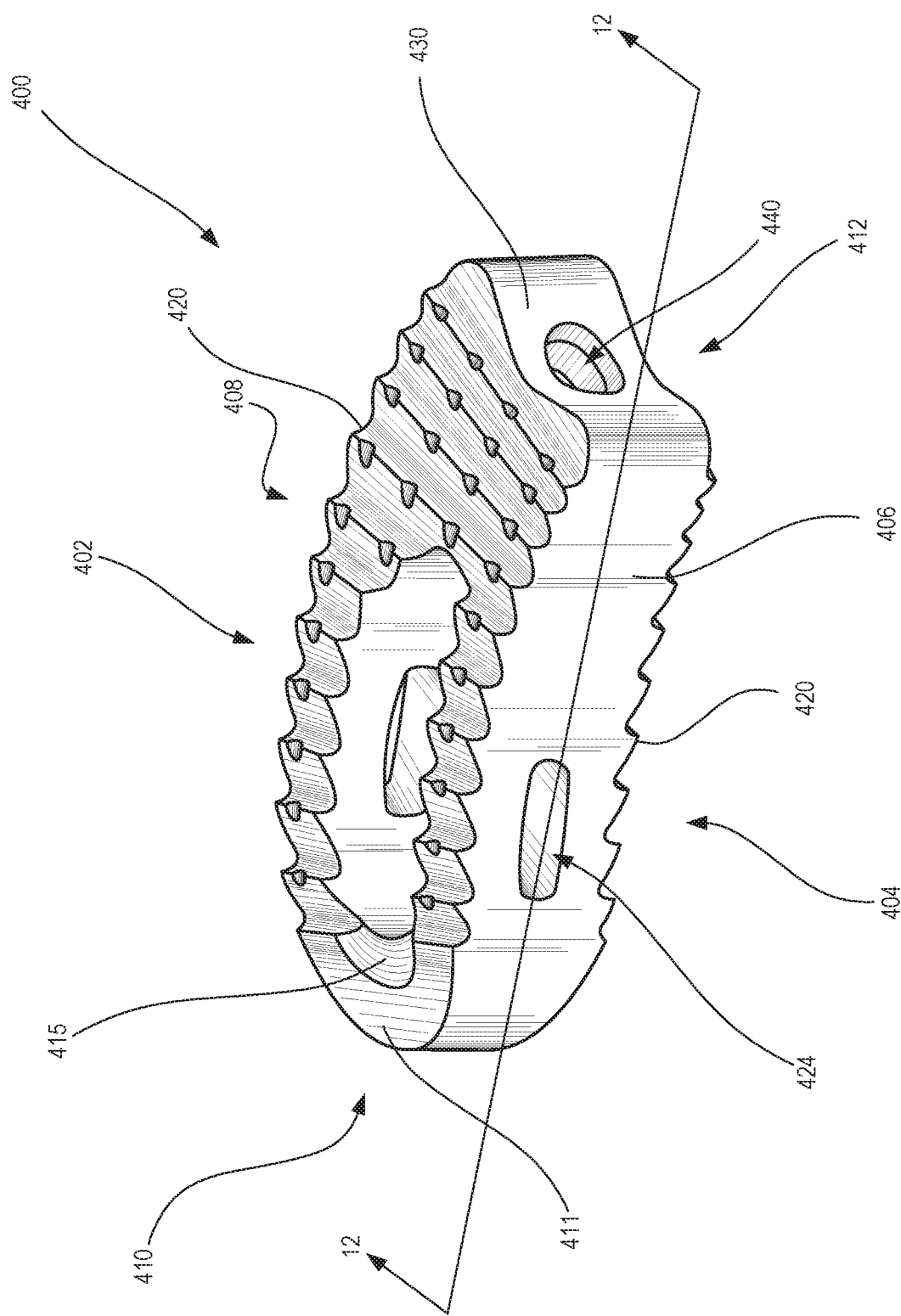
FIG. 10 is a perspective view of a spinal implant according to still another embodiment.
Figure 11:
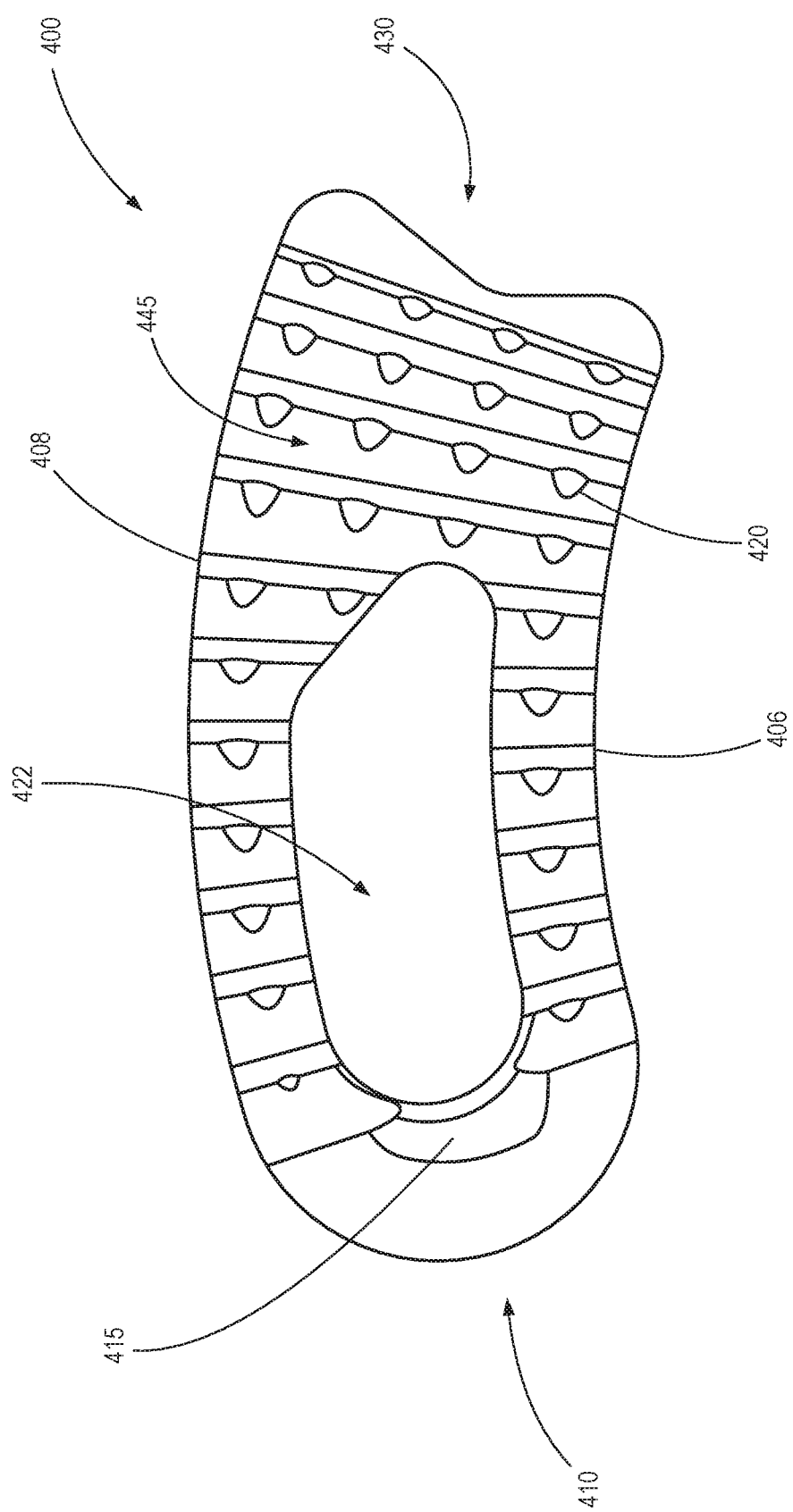
FIG. 11 is a top plan view of the spinal implant of FIG. 10.
Figure 12:
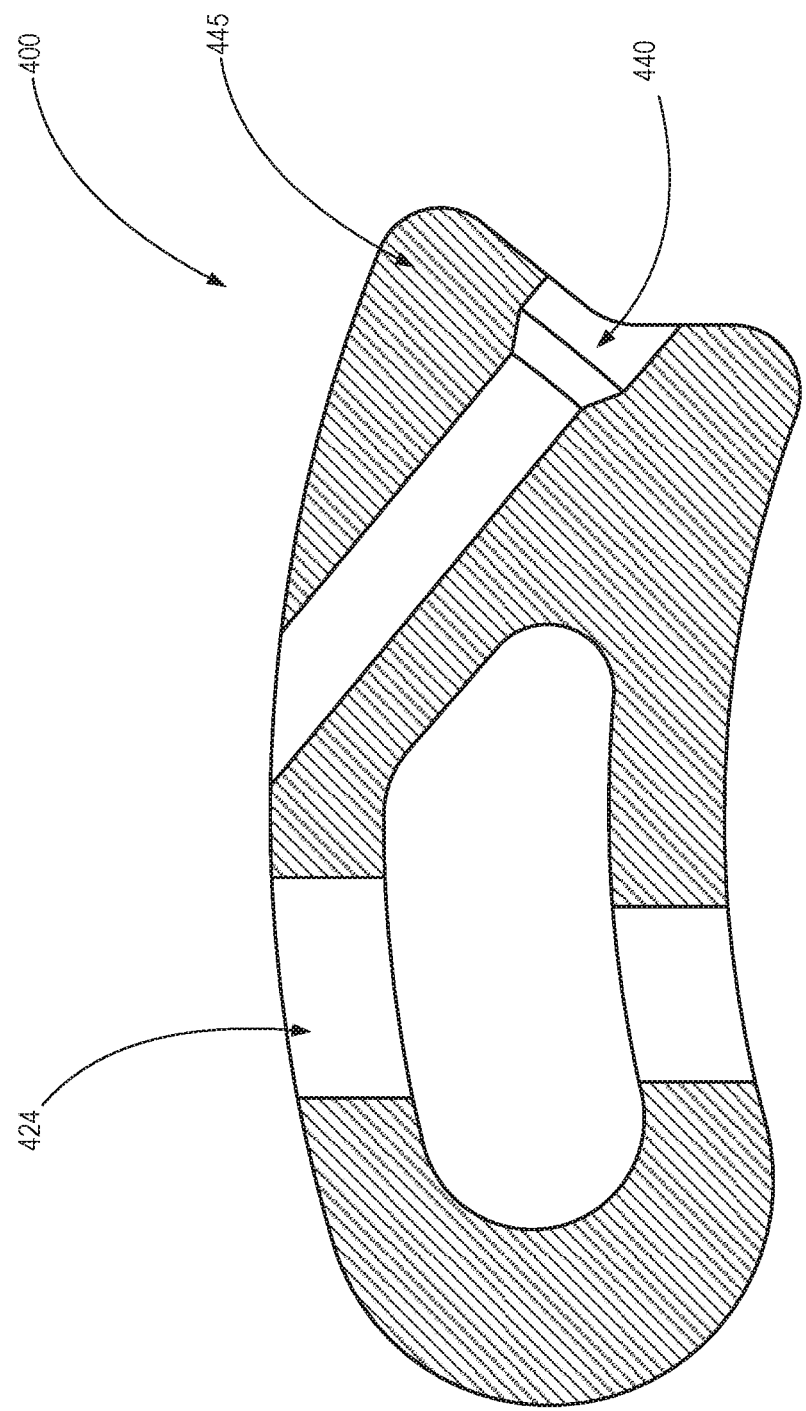
FIG. 12 is a cross-sectional view of the spinal implant of FIGS. 10 and 11.

FIG. 10 is a perspective view of a spinal implant 400 according to still another embodiment. FIG. 11 is a top plan view of the spinal implant 400 of FIG. 10. And FIG. 12 is a cross-sectional view of spinal implant 400. Spinal implant 400 is most similar to spinal implant 300. However, spinal implant 400 comprises an inserter reinforced region 445 and an elongated inserter opening 440. Inserter reinforced region 445 is configured to provide enhanced stability and strength for the interface between an inserter instrument and opening 440. Inserter reinforced region 445 also allows for accommodating a longer inserter opening 440, such that there is more contact/interface between the instrument and spinal implant 400.

Although opening 440 begins at a central location within fish-tailed recess 430 of spinal implant 400, like spinal implant 300, opening 440 does not extend along the arcuate axis of spinal implant 400. More specifically, opening 440 is positioned at an angle of about 25 degrees with respect to the arcuate axis of spinal implant 400. In preferred embodiments, it is expected that the angle at which the opening is formed with respect to the axis of implant 400 will be slightly larger than the corresponding angle of implant 400. Thus, in some embodiments, this angle may be between about 5 degrees and about 50 degrees. In some such embodiments, this angle may be between about 15 degrees and about 50 degrees. In some such embodiments, the angle at which the opening is formed with respect to the axis of the implant may be between about 20 degrees and about 30 degrees. Of course, as inferred above, in some embodiments, the inserter hole/opening may extend at least substantially along the axis of the implant. In other words, the angle referenced above may be about zero degrees.

It can also be seen in FIG. 12 that opening 440 extends through side wall surface 408, rather than extending into the central opening 422 that extends through upper surface 402 and lower surface 404. However, alternative embodiments are contemplated in which opening 440 may form a blind hole that is closed at one end and does not extend all of the way through the side wall surface 408 of implant 400. It can also be seen in FIGS. 10-12 that opening 422 has been reshaped from the oval shape of previous embodiments to accommodate reinforced region 445. Otherwise stated, reinforced region 445 protrudes into the space that opening 422 would have otherwise occupied.

Like several of the previously described embodiments, rear end wall surface 412 comprises a recess 430 that comprises a v shape formed in a fishtail configuration that may be configured to directly interface with a spinal installation instrument or to indirectly couple with an intermediary piece configured to directly interface with such an instrument.

Also like several of the previous embodiments, upper and lower surfaces 402 and 404, respectively, of implant 400 both comprise a plurality of teeth 420 arranged in rows. Teeth 420 radiate from a focal point positioned along the axis of spinal implant 400. In addition, spinal implant 400 and its axis extend along an arcuate path to form a kidney shape. Each of the rows in which teeth 420 are arranged is at least substantially perpendicular to both the first side wall surface 406 and the second side wall surface 408. In addition, like the embodiments depicted in the previous figures, the spacing between the rows of teeth decreases from the front end wall surface 410 or nose 411 to the rear end wall surface 412.

Unlike the previously described embodiments, spinal implant 400 comprises a single opening 424 formed in side wall surfaces 406 and 408. Like the shape of central opening 422, this is due to the presence of reinforced region 445 and the elongated inserter opening 440 formed therein.

Spinal implant 400 further comprises a nose 411 that tapers as it extends from side wall surfaces 406 and 408 to the tip of the implant along both the upper surface 402 and the lower surface 404 of spinal implant 400. Spinal implant 400 further comprises notches 415 formed in both opposite surfaces of nose 411 to, as described above, facilitate allowing the sidewalls/rails to assist in positioning the implant during installation.

Figure 13:
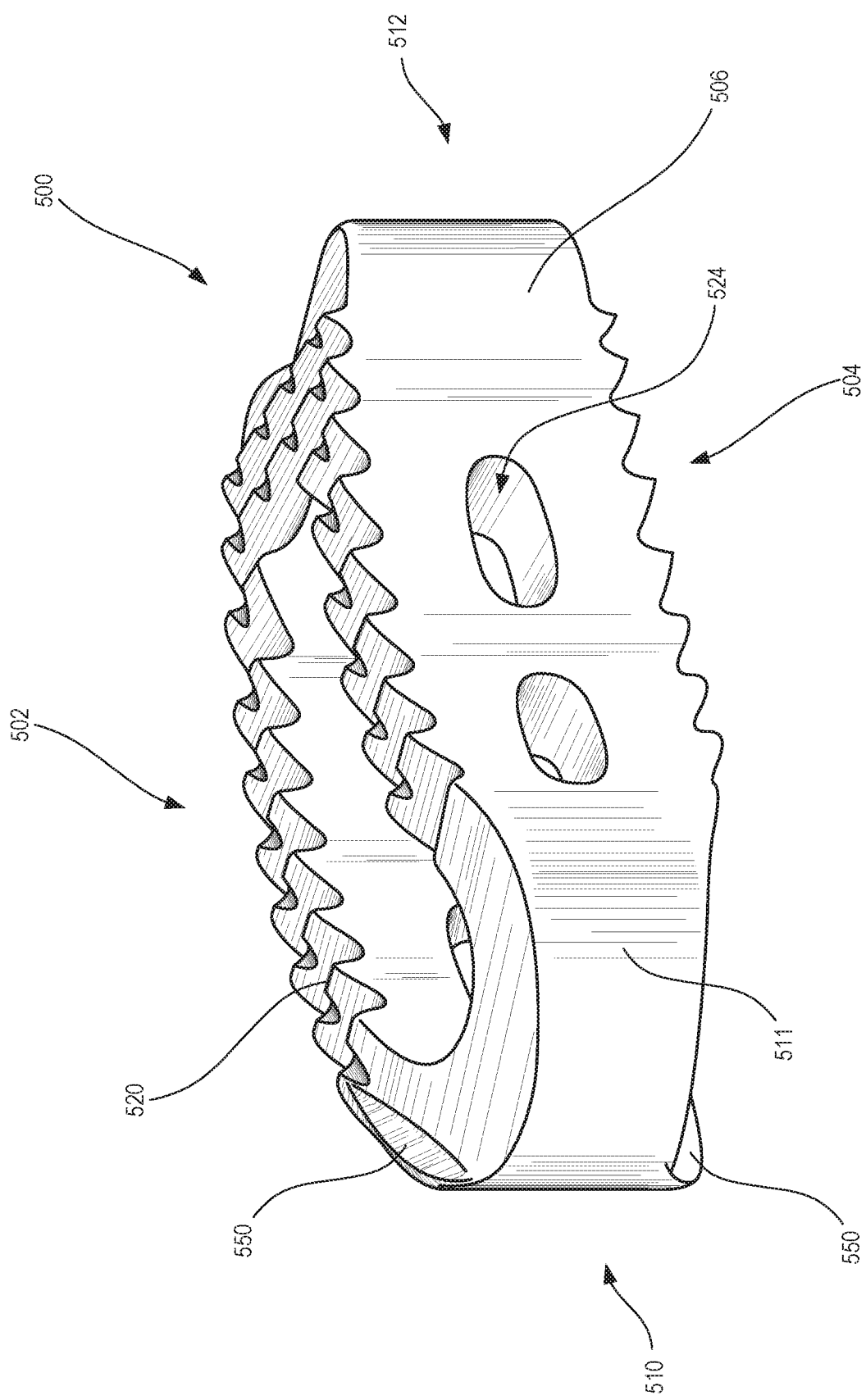
FIG. 13 is a perspective view of yet another embodiment of a spinal implant.
Figure 14:
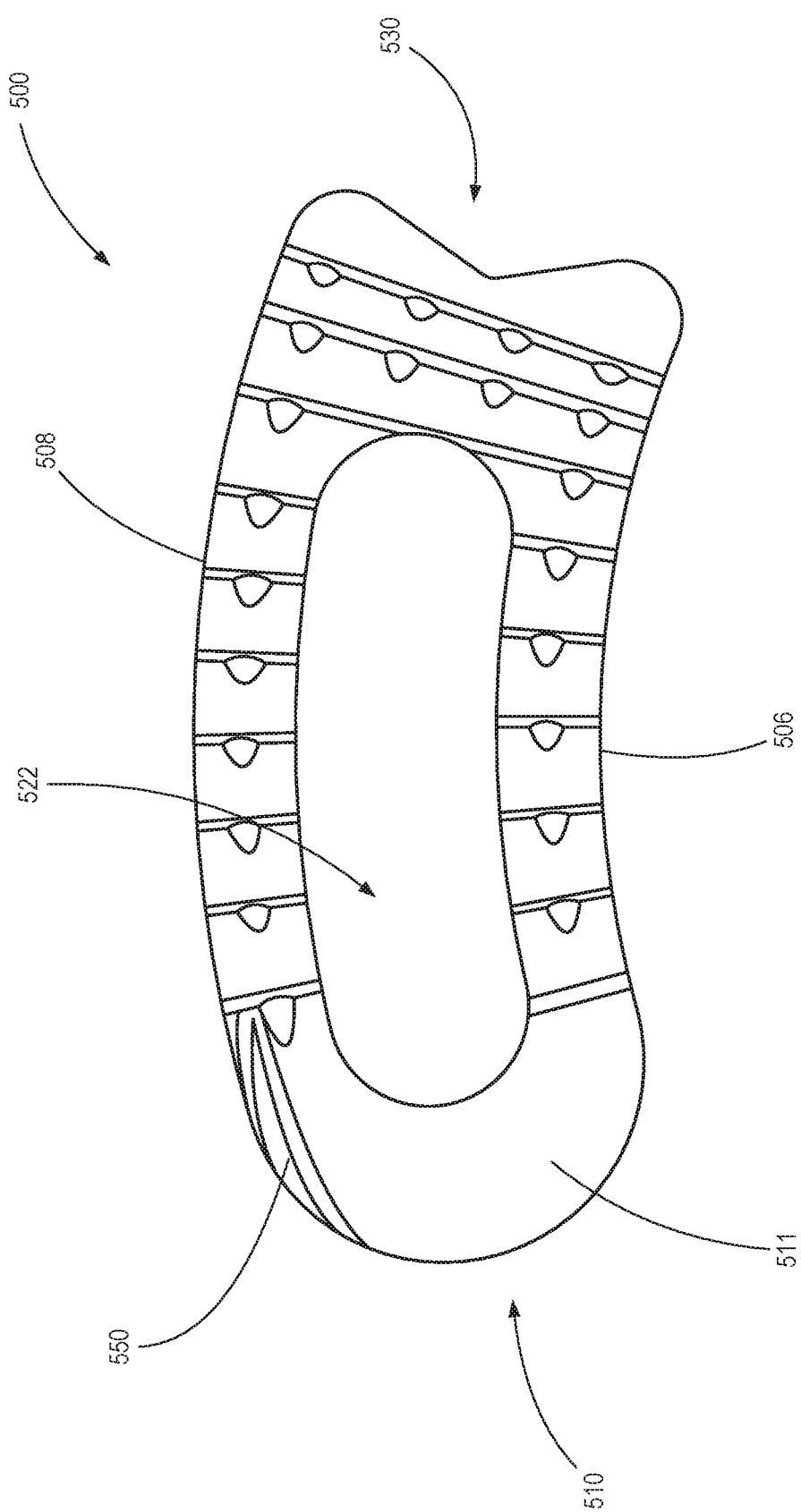
FIG. 14 is a top plan view of the spinal implant of FIG. 13.

FIG. 13 is a perspective view of yet another embodiment of a spinal implant 500. Spinal implant 500 is also depicted in the top plan view of FIG. 14. This embodiment comprises many of the same features and elements of embodiments previously described. For example, spinal implant 500 comprises an upper surface 502, a lower surface 504, a first side wall surface 506, a second side wall surface 508 opposite from surface 506, a front end wall surface 510 comprising a tapered nose 511, and a rear end wall surface 512 opposite from front end wall surface 510.

Rear end wall surface 512 comprises a v-shaped or fishtail recess 530 that may be configured to directly interface with a spinal installation instrument or to indirectly couple with an intermediary piece configured to directly interface with such an instrument. Although not shown in FIGS. 13 and 14, spinal implant 500 may also comprise an opening formed in v-shaped recess 530. In some embodiments, such opening may be threaded so as to allow for engagement with an inserter tool. This inserter opening may extend along the arcuate axis of spinal implant 500 or, alternatively, may extend at an angle with respect to this axis as previously described. Also, this opening may form a blind hole that is closed at one end, may extend through central opening 522, or may extend through one of the side wall surfaces of the implant.

Like each of the embodiments described above, upper and lower surfaces 502 and 504 of implant 500 both comprise a plurality of teeth 520 arranged in rows. Also, as mentioned above, upper surface 502 comprises an opening 522 that extends through lower surface 504 and openings 524 are formed in side wall surfaces 506 and 508. Spinal implant 500 further comprises a nose 511 that tapers as it extends from side wall surfaces 506 and 508 to the tip of the implant along both the upper surface 502 and the lower surface 504 of the implant.

However, instead of the notches described above that were formed in both opposite surfaces of the nose, spinal implant 500 comprises partial fins 550 positioned on the upper and lower surfaces of nose 511. It has been discovered that providing fins 550, or any of the alternative fins described herein, may be useful in facilitating installation of the implant upon which such fins are positioned. More particularly, such fins may facilitate guiding the implant in a curved path as it is installed in a patient's intervertebral space.

Fins 550 are positioned along only the convex side wall surface 508. However, other embodiments are contemplated in which fins are also positioned along concave side wall surface 506. Fins 550 are also only positioned along a portion of front end wall surface 510 and adjacent nose 511 beyond the first row of teeth 520. In addition, as shown in both FIG. 13 and FIG. 14, fins 550 are contiguous with and extend from the convex surface forming nose 511.

However, as will be discussed below in connection with other embodiments, such fins may also extend alongside the teeth across the entire length of the spinal implant if desired. In addition, although not depicted in any figures, other embodiments are contemplated in which fins 550 extend further than they are depicted as extending in FIGS. 13 and 14, but do not extend across the entire length of the implant. For example, fins 550 may extend halfway across the length of spinal implant 500, or any other length as desired. The upper surface of the upper fin, and the lower surface of the lower fin, may also taper towards the tip of nose 511 in a similar manner as nose 511 tapers towards this tip along both its upper and lower surfaces.

Figure 15:
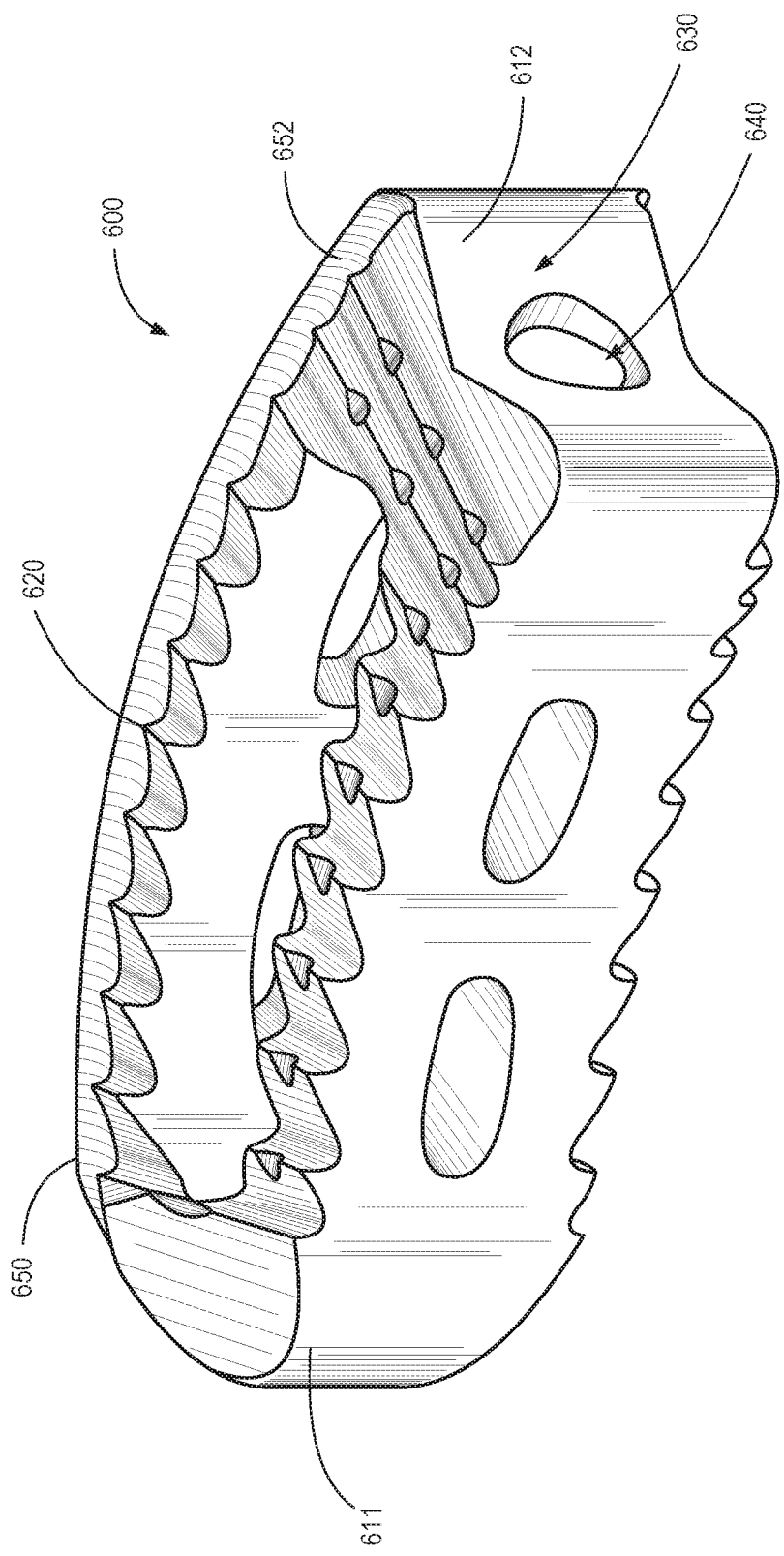
FIG. 15 is a perspective view of still another embodiment of a spinal implant.
Figure 16:
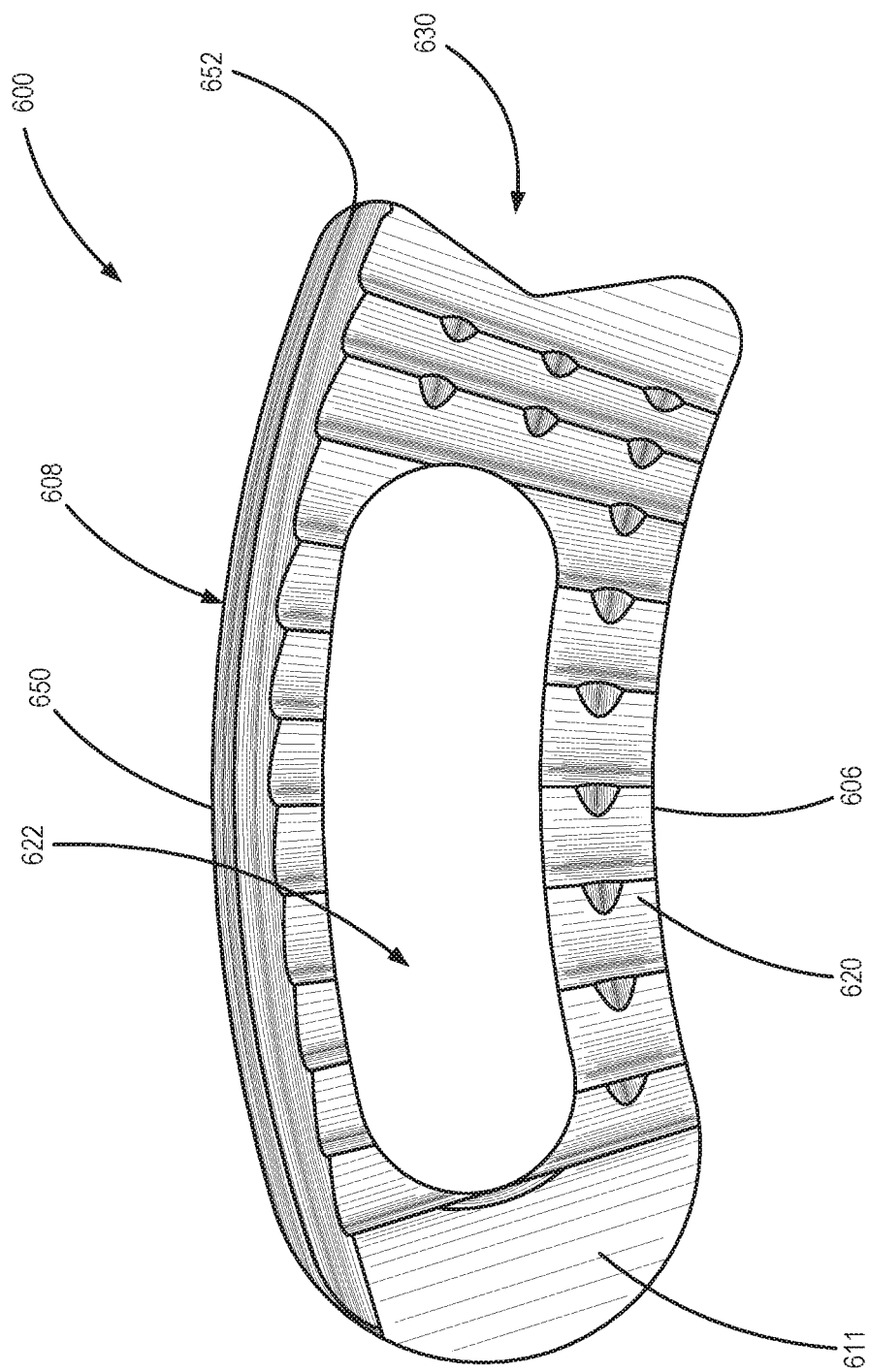
FIG. 16 is a top plan view of the embodiment of FIG. 15.

FIG. 15 is a perspective view of still another embodiment of a spinal implant 600. FIG. 16 depicts a top plan view of spinal implant 600. Spinal implant 600 is identical to spinal implant 500 other than the configuration of its fin 650. Unlike fin 550, fin 650 extends across the entire length of spinal implant 600 along its convex sidewall surface 608. Fin 650 also extends along a portion of tip 611 that is contiguous with sidewall surface 608. In some embodiments, an additional fin may extend along concave sidewall surface 606 if desired, although the depicted embodiment lacks such a fin.

In addition, in order to accommodate fin 650 alongside teeth 620 on the convex side of implant 600, a channel 652 is formed in between fin 650 and teeth 620. In some embodiments, fin 650 may be configured to extend no further than about the same height as teeth 620. Alternatively, fin 650 may extend beyond the height of the profile of teeth 620 for certain applications.

As still other alternatives, the fin may comprise a discontinuous fin comprising multiple fin portions interspersed by regions in which no fin is present, and/or regions in which the fin is shorter or taller. Similarly, the fin(s) may otherwise change in geometry/shape—such as changes in thickness, height, sharpness, etc.—at one or more portions/positions along the fin(s).

Preferably, the fin does not extend all the way to the tip of the nose of the implant. This may be useful in order to allow the nose to be used to pry open the intervertebral space or otherwise facilitate implantation of the device. For example, with respect to spinal implants 500 and 600, their respective fins 550 and 650 terminate at about the point at which the curvature of the tip increases such that the distal-most portion of the tip does not comprise a fin. In addition, although both fins 550 and 650 are shown extending along the outer surface of the convex sidewall, other embodiments are contemplated in which the fins may instead be positioned along an interior surface of the convex sidewall (and/or the opposite concave sidewall) that defines central opening 622. However, the positioning shown in the figures (along the outer surface of the sidewall) is thought to be preferable for most applications.

As with several previous embodiments, rear end wall surface 612 of implant 600 comprises a v-shaped or fishtail recess 630 that may be configured to directly interface with a spinal installation instrument or to indirectly couple with an intermediary piece configured to directly interface with such an instrument. Spinal implant 600 may further comprise an opening 640 formed in v-shaped recess 630 that may be threaded so as to allow for engagement with an inserter tool. This opening, as discussed above, may extend along the arcuate axis of spinal implant 600 or, alternatively, may extend at an angle with respect to this axis. Also, this opening may form a blind hole that is closed at one end, may extend through central opening 622, or may extend through one of the side wall surfaces of implant 600.

Figure 17:
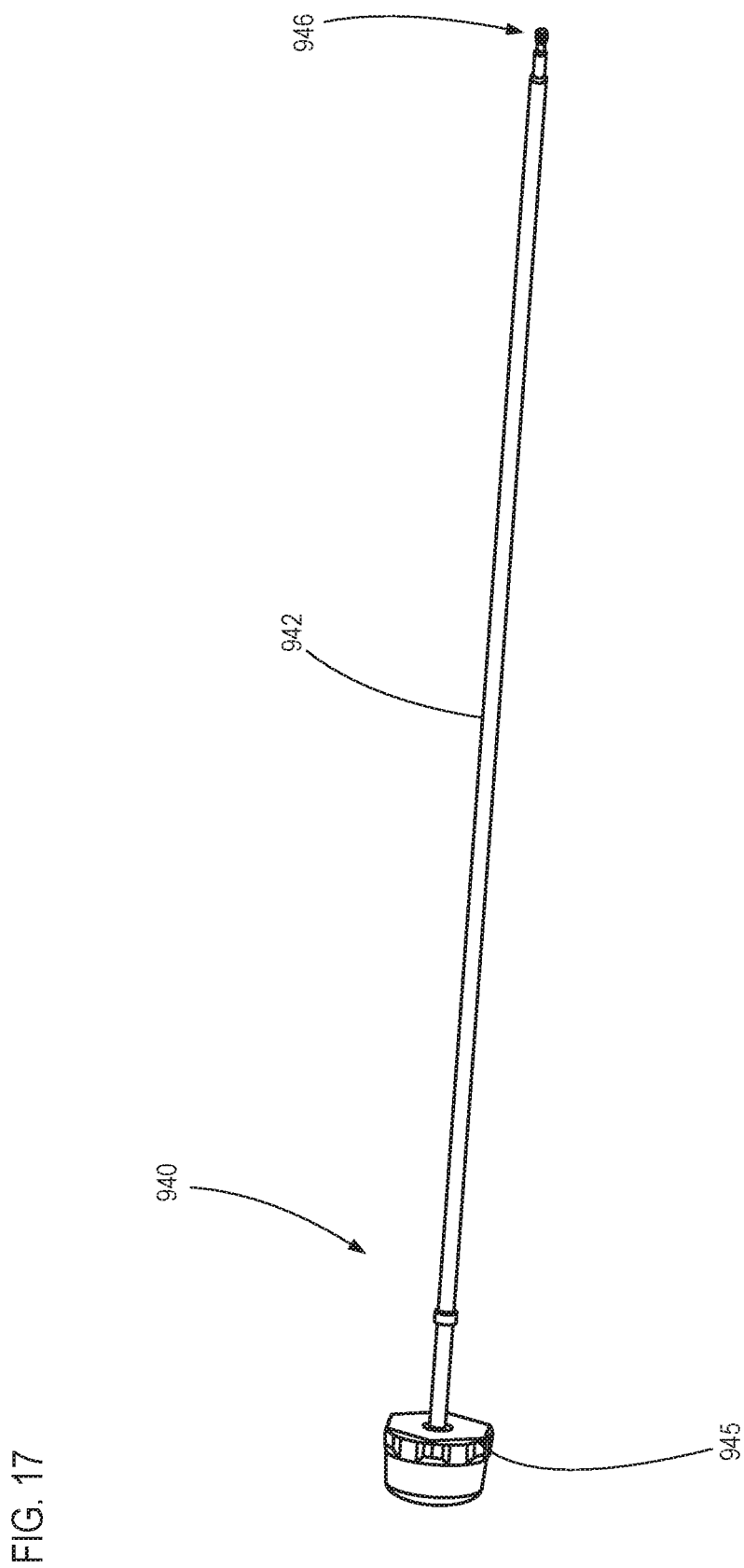
FIG. 17 depicts an embodiment of an installation rod configured to be positioned within certain embodiments of surgical instruments for installing spinal implants.

FIG. 17 depicts an embodiment of a hub 940 comprising an installation rod 942 configured to be used with certain embodiments of surgical instruments for installing spinal implants, and to be coupled with certain embodiments of spinal implants. Hub 940 comprises a handle 945, which may comprise a plurality of knobs configured to facilitate gripping and rotation by a surgeon. Installation rod 942 further comprises a distal tip 946.

Figure 18:
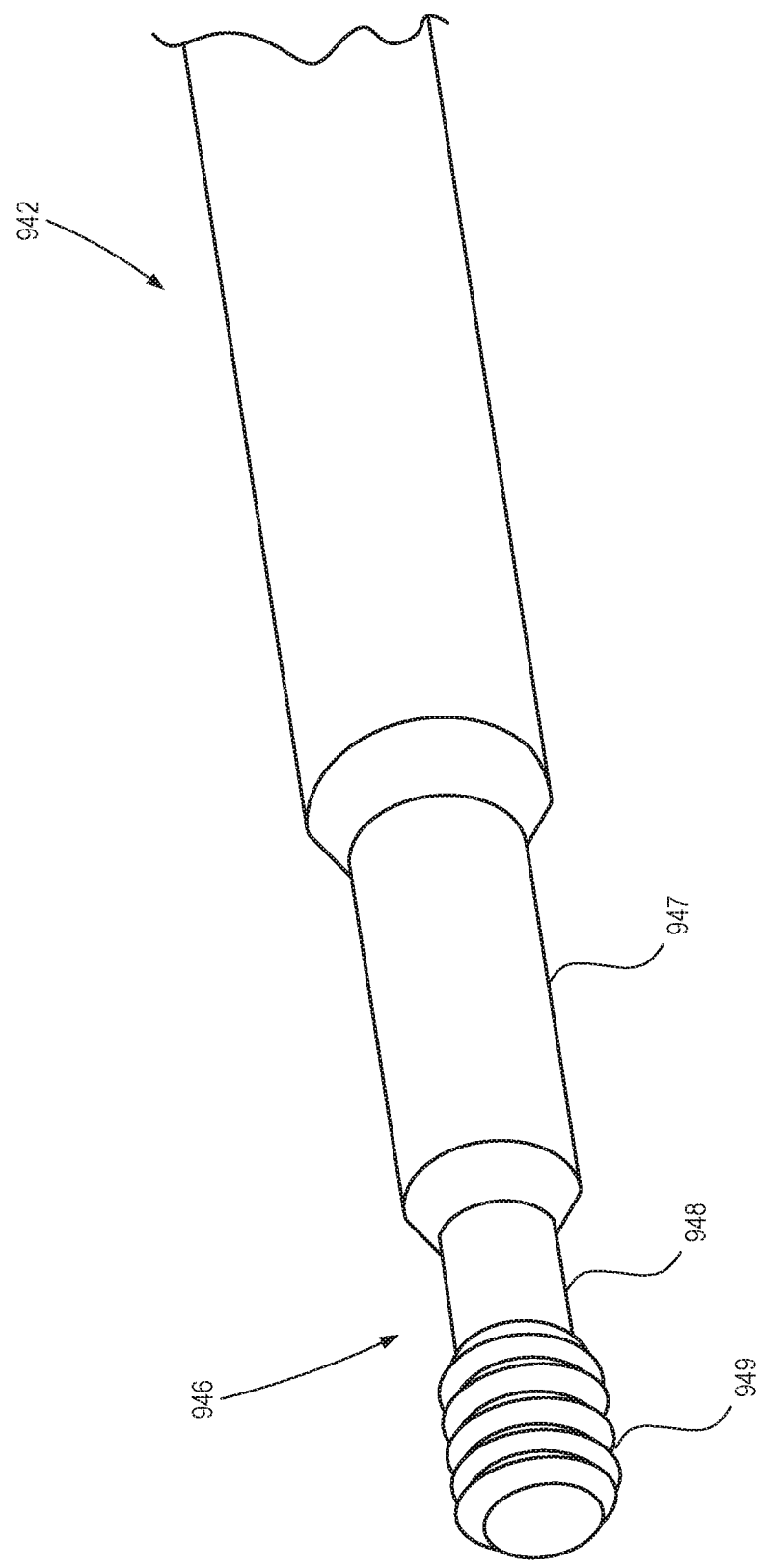
FIG. 18 is a close-up view of the distal end of the installation rod of FIG. 17 that is configured to interface with a spinal implant.

As depicted in the close-up view of FIG. 18, distal tip 946 comprises two separate reduced diameter regions—namely, a first reduced diameter region 947 and a second reduced diameter region 948—and a threaded portion 949 positioned adjacent to the second reduced diameter region 948. Preferably, reduced diameter region 948 that is positioned adjacent to threaded portion 949 provides clearance with at least one thread of a threaded hole of a corresponding implant. This may be useful in providing for offloading of the stress/forces on this thread or threads.

As shown in FIG. 18, second reduced diameter region 948 comprises a diameter that is less than the threads of threaded portion 949. In addition, first reduced diameter region 947 comprises a diameter that is substantially identical to, or slightly less than, the diameter of the threads of threaded portion 949, such that it can be received in the opening of a threaded spinal implant hole.

However, alternative embodiments are contemplated in which only one reduced diameter region is provided adjacent to the threaded portion 949. In some such embodiments, the entire portion of distal tip 946 proximal to second reduced diameter region 948 may be slightly less than or substantially identical to the diameter of the threads of threaded portion 949.

It has been discovered that providing a reduced diameter region adjacent to a threaded tip may provide substantial benefits, particularly with respect to ceramic spinal implants, such as silicon nitride ceramic spinal implants, for example. To elaborate, providing such a reduced diameter region ensures that the highest forces applied to threads in the spinal implant will be applied to the strongest threads. This may substantially reduce fractures or other damage that may otherwise occur with respect to the spinal implant. In some embodiments and implementations, this configuration may allow for threaded engagement only with full threads of the implant, as opposed to partial threads. Since the threads at the opening of a threaded hole tend to be partial threads that are less strong, providing a reduced diameter region immediately adjacent to a threaded tip of an insertion rod may allow for bypassing engagement with these weaker threads in favor of engagement of the full, stronger threads that are typically deeper within the body of the implant. Thus, by using the principles of the embodiment depicted in FIG. 18, the only threaded engagement between rod 942 and a threaded opening of a spinal implant may be positioned at a spaced location from the periphery of the opening of a threaded hole such that there is no engagement between rod 942 and the partial threads at the opening of this hole.

Figure 19:
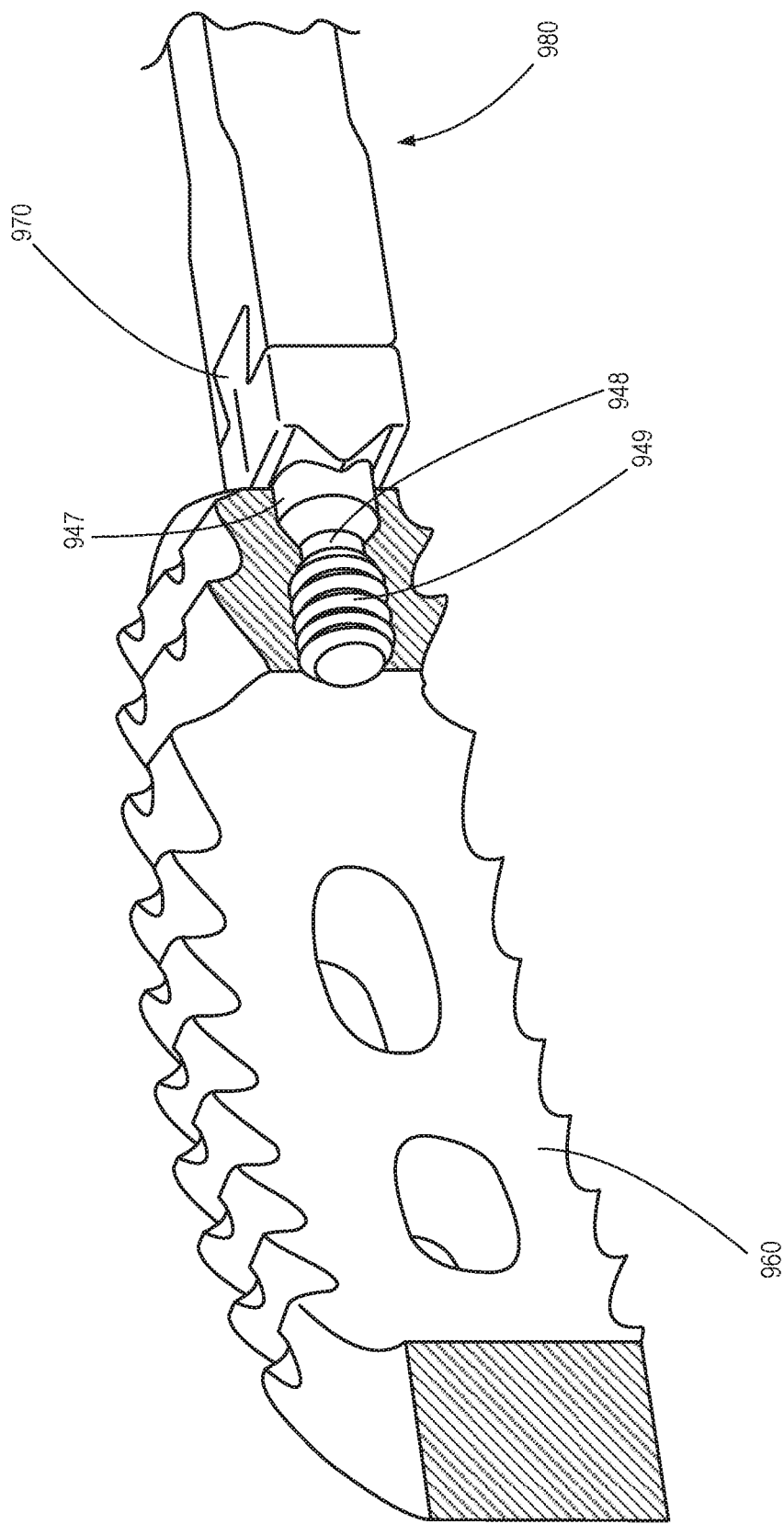
FIG. 19 depicts embodiments of a spinal implant, an inserter, and an intermediary piece each positioned in engagement with one another and specifically depicting the interface between the installation rod of FIG. 17 and a spinal implant.

FIG. 19 depicts embodiments of a spinal implant, an inserter, and an intermediary piece each positioned in engagement with one another and specifically depicting the interface between the installation rod 942 of FIGS. 17 and 18 and a spinal implant 960. As shown in this figure, an inserter 980 is coupled with an intermediary piece 970, which is positioned in between inserter 980 and spinal implant 960. Intermediary piece 970 comprises a protrusion positioned on a first side of the intermediary piece that is configured to mate and fit within corresponding recess formed within a distal end of inserter 980. Similarly, intermediary piece 970 comprises a protrusion positioned on an opposite second side of intermediary piece 970 opposite from the first side, which mates with a fishtail recess of spinal implant 960.

In some preferred embodiments, intermediary piece 970 comprises a non-ceramic material, such as PEEK, titanium, or other such materials known to those of ordinary skill in the art.

It should be understood that, although intermediary piece 970 is shown as a separate element that is configured to couple with inserter 980, other embodiments are contemplated in which intermediary piece 970 is an integral part of inserter 980, or in which inserter 980 otherwise comprises a shape at its distal end matching, or similar to, the distal end of intermediary piece 970.

As best seen from the view of FIG. 19, threaded portion 949 of rod 942 only engages a threaded portion of spinal implant 960 within the body of spinal implant 960. Due to the presence of reduced diameter region 948, which is preferably unthreaded and set back from the rear end of spinal implant 960, as shown in FIG. 19, there is no engagement between the partial threads adjacent to the opening of the threaded hole of spinal implant 960 and rod 942. In some embodiments, the threaded section of spinal implant 960 may be positioned in the thickest part of spinal implant 960 so as to further facilitate a desirable engagement that reduces the chances of breakage, particularly when certain ceramic materials are used to form the implant.

Figure 20:
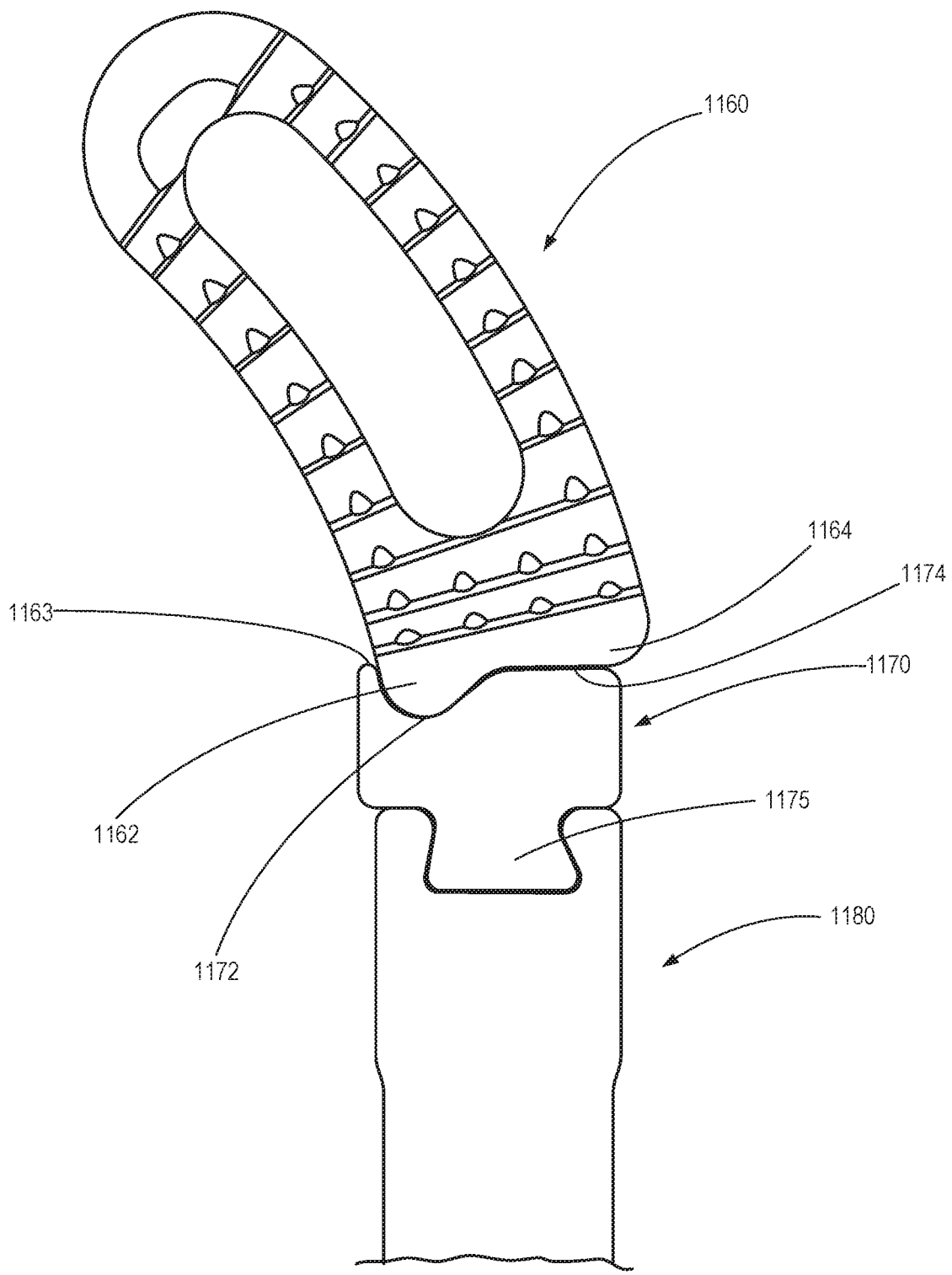
FIG. 20 depicts alternative embodiments of a spinal implant, an inserter, and an intermediary piece each positioned in engagement with one another.

FIG. 20 depicts further embodiments of a spinal implant 1160, an inserter 1180, and an intermediary piece 1170 each positioned in engagement with one another. More particularly, inserter 1180 is coupled with intermediary piece 1170, which is positioned in between inserter 1180 and spinal implant 1160. Intermediary piece 1170 comprises a protrusion 1175 positioned on a first side of intermediary piece 1170 that is configured to mate and fit within a corresponding recess formed within a distal end of inserter 1180. Similarly, intermediary piece 1170 comprises a surface positioned on a second side of intermediary piece 1170 opposite from the first side, which mates with a rear end of spinal implant 1160.

It should be understood that, although intermediary piece 1170 is shown as a separate element that is configured to couple with inserter 1180, other embodiments are contemplated in which intermediary piece 1170 is an integral part of inserter 1180, or in which inserter 1180 otherwise comprises a shape at its distal end matching, or similar to, the distal end of intermediary piece 1170.

Spinal implant 1160 comprises a rear end that has a non-symmetrical shape. More particularly, the rear end of spinal implant 1160 comprises a non-symmetrical fishtail shape. This shape is formed by a first rounded protrusion 1162 extending from a lateral side of implant 1160 at the rear end. A second protrusion 1164 may be formed at the opposite lateral side of implant 1160 if desired. In the depicted embodiment, second protrusion 1164 is configured to be at least substantially parallel to an interface of inserter 1180 and/or intermediary piece 1170.

Thus, as shown in FIG. 20, intermediary piece 1170 comprises a shape at its distal end that is at least substantially complementary to that of the rear end of spinal implant 1160 so as to allow for these two surfaces to mate with one another. Intermediary piece 1170 therefore comprises a recess 1172 matching the first protrusion 1162 and an at least substantially planar surface 1174 configured to match one of the surfaces defining second protrusion 1164. In the depicted embodiment, surface 1174 is at least substantially perpendicular to the direction with which inserter 1180 extends. However, other embodiments are contemplated in which this need not be the case. For example, in other contemplated embodiments, second protrusion 1164 may extend into a concave recess similar to recess 1172 on the opposite side of recess 1172.

It can also be seen in FIG. 20 that intermediary piece 1170 comprises a lip 1163 that extends slightly around a lateral surface of spinal implant 1160. Although, in alternative embodiments, this lip 1163 may extend along a greater extent of this lateral surface (in some embodiments the entire length), it has been discovered that for certain implant materials, such as silicon nitride ceramic materials, only a very small lip or, as discussed below, in some cases no lip at all, may be needed in order to provide suitable stability for a surgical procedure. In this particular embodiment, lip 1163 does not extend further than the profile of surface 1174 of intermediary piece 1170.

Figure 21:
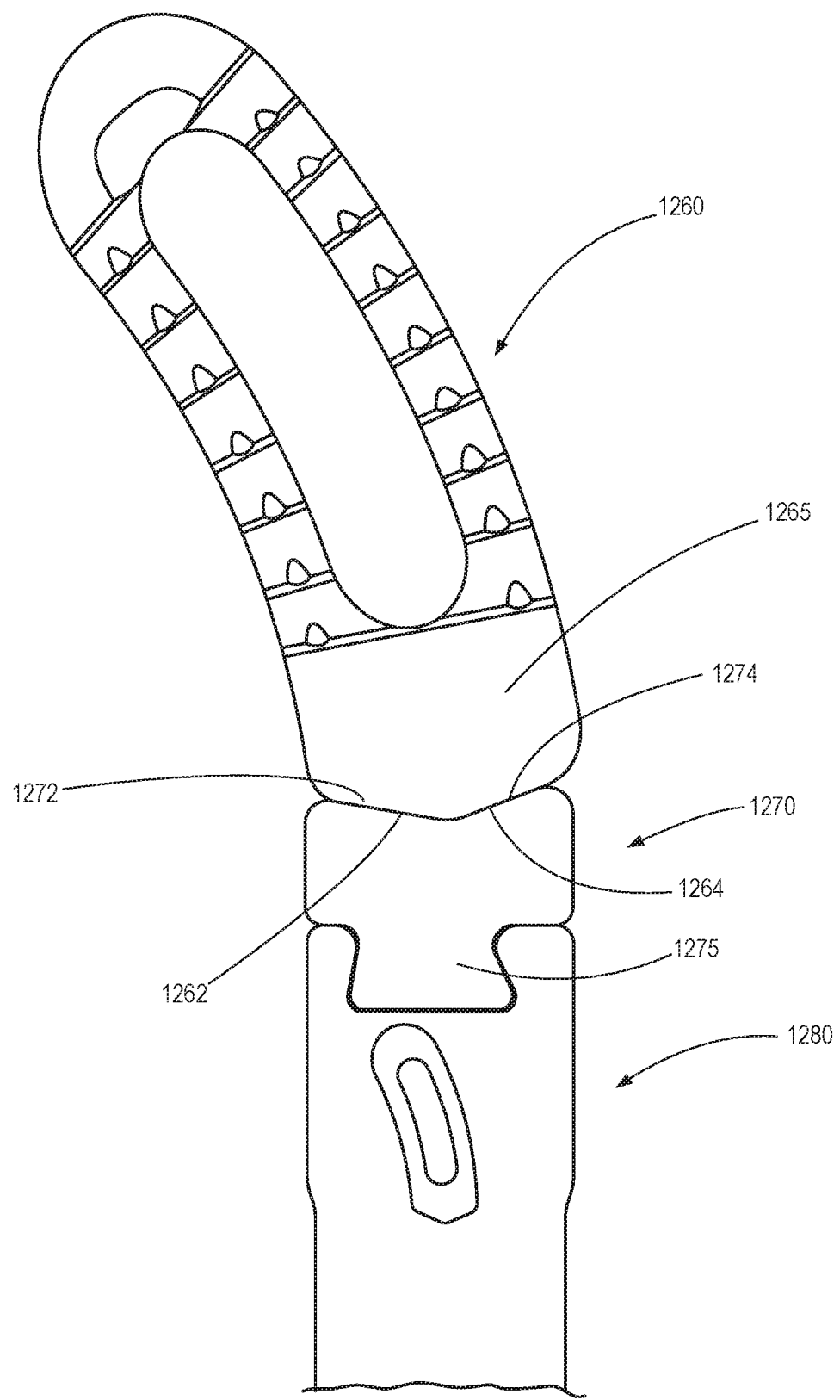
FIG. 21 depicts other embodiments of a spinal implant, an inserter, and an intermediary piece each positioned in engagement with one another.

FIG. 21 depicts still further embodiments of a spinal implant 1260, an inserter 1280, and an intermediary piece 1270 each positioned in engagement with one another. More particularly, inserter 1280 is coupled with intermediary piece 1270, which is positioned in between inserter 1280 and spinal implant 1260. Intermediary piece 1270 comprises a protrusion 1275 positioned on a first side of intermediary piece 1270 that is configured to mate and fit within a corresponding recess formed within a distal end of inserter 1280. Similarly, intermediary piece 1270 comprises a recess positioned on an opposite second side of intermediary piece 1270 opposite from the first side, which mates with a rear end of spinal implant 1260.

Spinal implant 1260 differs from spinal implant 1160 in that the rear surface of spinal implant 1260 comprises a v-shaped protrusion. This protrusion is formed from surface 1262 and surface 1264, both of which are at least substantially flat. Also, this protrusion is non-symmetrical. More particularly, surface 1262 is longer than surface. 1264. Non-symmetrical mating surfaces, such as are present in spinal implants 1160 and 1260, may be useful for a variety of reasons. For example, a non-symmetrical surface may be useful to ensure that the implant is engaged with an intermediary piece or inserter in the desired position only. In other words, if you turn the implant upside down, it will not properly engage with the complementary mating surface on the inserter or intermediary piece.

This lack of symmetry may also be present on the intermediary piece. For example, as shown in FIG. 21, intermediary piece 1270 comprises a protrusion 1275 that is not centered with respect to a corresponding inserter 1280. Thus, intermediary piece 1270 may only be correctly engaged with inserter 1280 if the right side of intermediary piece 1270 is positioned upwards.

Intermediary piece 1270 also comprises a v-shaped recession that is non-symmetrical and that is configured to engage the v-shaped protrusion on spinal implant 1260. More particularly, intermediary piece 1270 comprises a v-shaped recess defined by a first flat surface 1272 and a second flat surface 1274 angled with respect to the first flat surface 1272. Surface 1272 is complementary to surface 1262 of implant 1260 and surface 1274 is complementary to surface 1264 of implant 1260, as shown in FIG. 21.

It can also be seen in FIG. 21 that intermediary piece 1270 differs from intermediary piece 1170 in that it is configured to engage with spinal implant 1260 without extending beyond the profile of spinal implant 1260 immediately adjacent to intermediary piece 1270. In other words, the opposing lateral surfaces of intermediary piece 1270 are aligned with the opposing lateral surfaces of spinal implant 1260 immediately adjacent to intermediary piece 1270 when spinal implant 1260 is engaged with intermediary piece 1270. In some embodiments, the distal portion of an inserter may alternatively, or additionally, be similarly configured to avoid extending beyond the profile of the spinal implant immediately adjacent to the inserter. In some embodiments, the inserter and/or intermediary piece may also, or alternatively, be configured such that the corresponding implant does not extend beyond the height of the inserter and/or intermediary piece. Thus, some embodiments may be configured such that the implant does not extend beyond the profile of the distal portion of the inserter and/or intermediary piece in any view, including an upper view and a side view.

Although in this particular embodiment, the opposing lateral surfaces of spinal implant 1260 are at least substantially aligned with the end of the inserter or intermediary piece, alternative embodiments are contemplated in which the opposing lateral surfaces of spinal implant 1260 are less than the corresponding opposing surfaces of the inserter or intermediary piece. In other words, the inserter and/or intermediary piece may comprise a width at a distal end that is greater than or equal to the corresponding width of the spinal implant to be used with the inserter/intermediary piece.

Of course, alternative embodiments are contemplated in which this same feature may be obtained without providing an intermediary piece. For example, an inserter may be provided having a shape/surface at its distal end identical or similar to the distal surface of an intermediary piece without need for providing the intermediary piece.

Spinal implant 1260 also comprises a portion 1265 positioned along a rear portion of its top surface that lacks teeth, as shown in FIG. 21. This may be useful for certain applications in order to preserve desired structural integrity for certain procedures. However, other embodiments, such as spinal implant 1160 of FIG. 20, may comprise teeth that extend all the way to the rear end of the implant. In some embodiments, this smooth portion 1265 may comprise a thickness at least substantially identical to the maximum thickness of the implant 1260 at the tips of the teeth.

Figure 22:
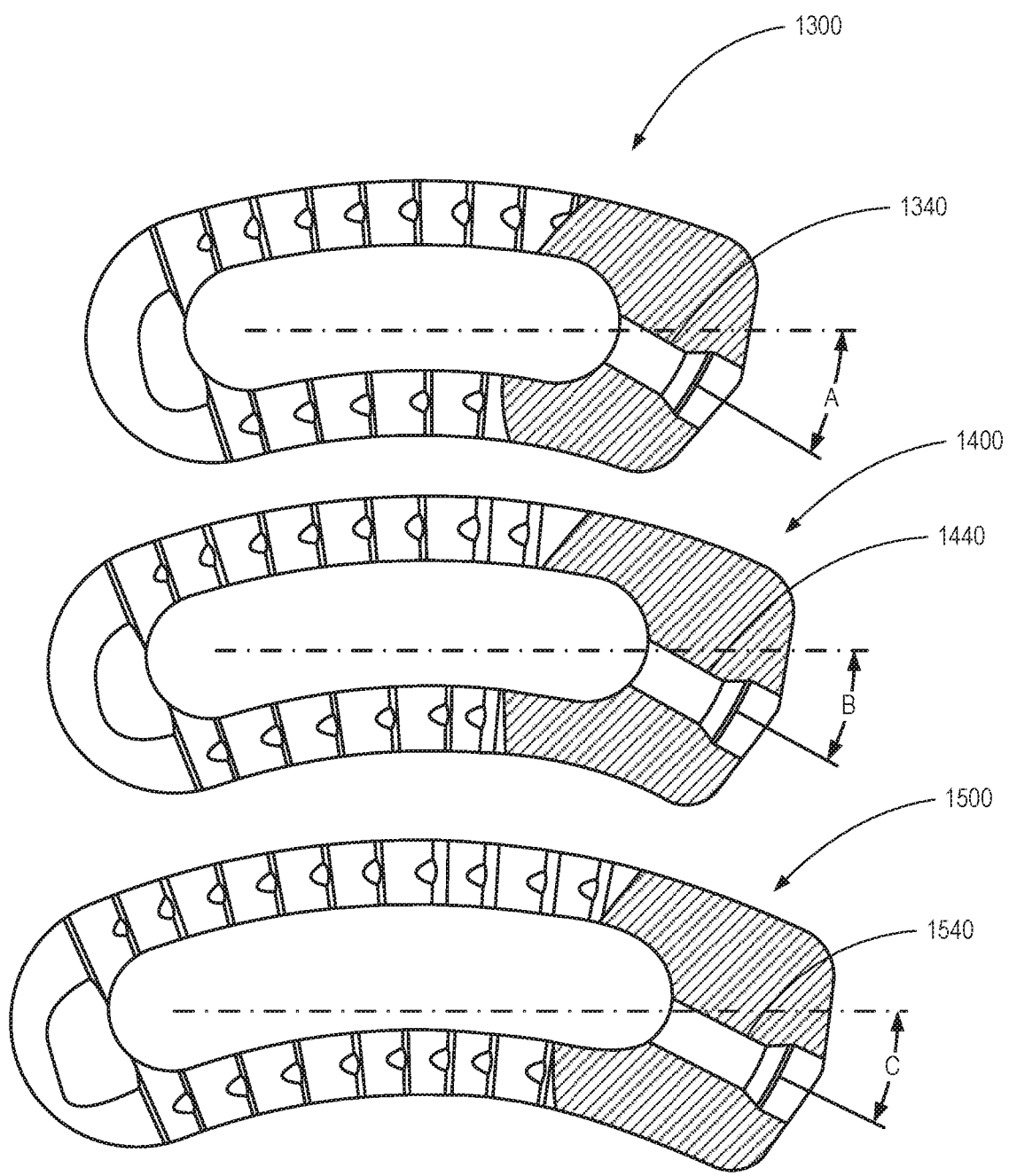
FIG. 22 is a partial, cross-sectional view of three embodiments of spinal implants each having different sizes and different inserter hole angles.

FIG. 22 depicts three additional embodiments of spinal implants—namely, spinal implants 1300, 1400, and 1500. These three spinal implants vary in size and in the angling of their respective inserter holes—inserter holes 1340, 1440, and 1540, respectively. More particularly, inserter hole 1340 extends at an angle "A" with respect to a central axis of implant 1300, inserter hole 1440 extends at an angle "B" with respect to a central axis of implant 1400, and inserter hole 1540 extends at an angle "C" with respect to a central axis of implant 1500.

In some preferred embodiments and/or systems incorporating multiple spinal implants of different sizes, these angles become smaller as the size of the implant increases. Thus, with regard to the three embodiments depicted in FIG. 22, angle A is greater than angle B and angle B is greater than angle C. This may be useful for keeping the implant/inserter profile within a maximum width to allow for inserting any of the various implants within a tube of a given diameter.

In some embodiments, for an implant having a 10×27 mm profile (width v. length), angle A may be between about 25 and about 35 degrees. In some such embodiments, angle A may be about 30 degrees. In some embodiments, for an implant having a 10×30 mm profile, angle B may be between about 23 and about 33 degrees. In some such embodiments, angle B may be about 28 degrees. In some embodiments, for an implant having a 10×33 mm profile, angle C may be between about 20 degrees and about 30 degrees. In some such embodiments, angle C may be about 25 degrees. In some embodiments, the angle (A/B/C) of the inserter hole may therefore decrease at least substantially in proportion to an increase in length of the implant and/or at least substantially in proportion to a decrease in the radius of curvature of the implant.

Figure 23:
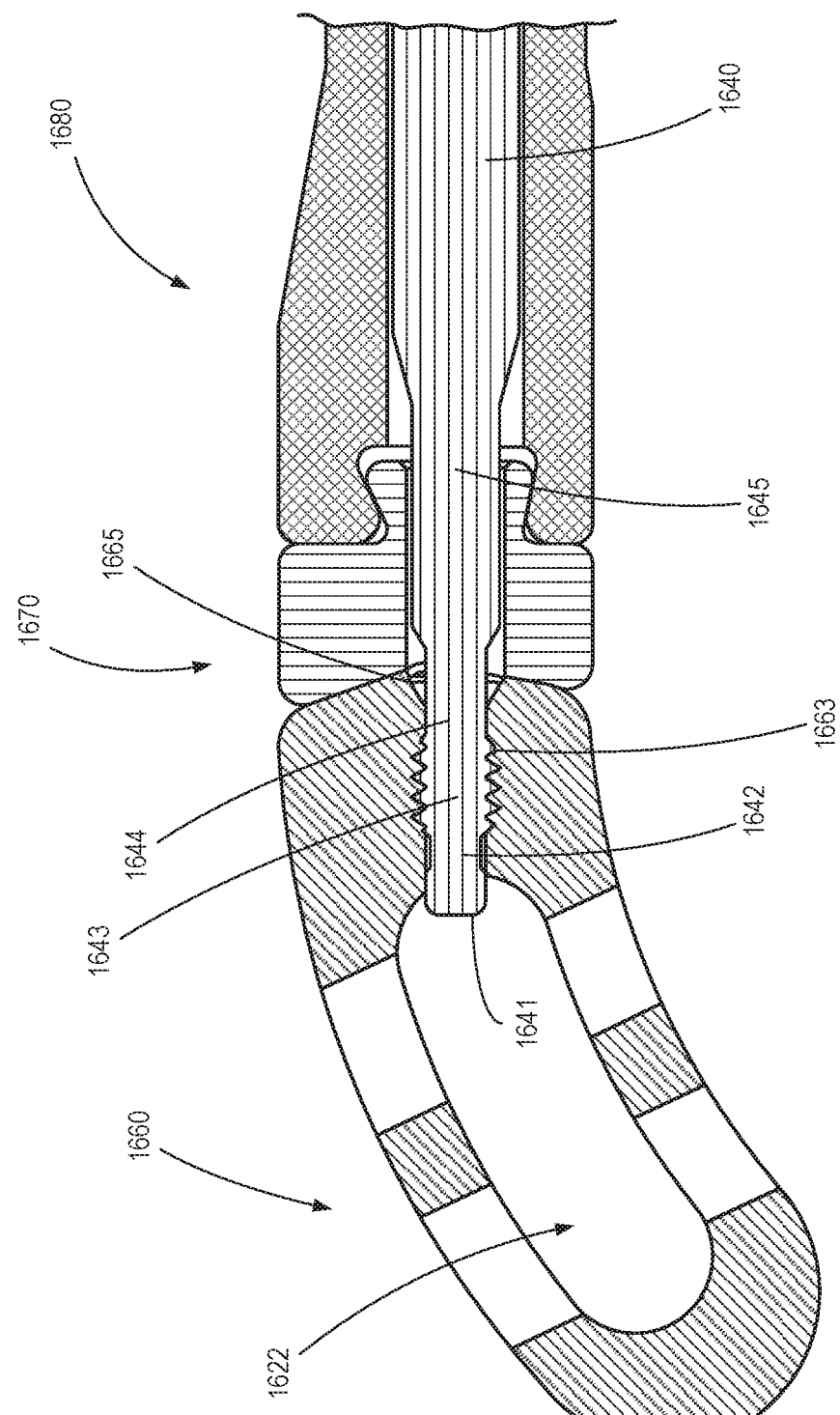
FIG. 23 is cross-sectional view of still other alternative embodiments of a spinal implant, an inserter, and an intermediary piece each positioned in engagement with one another.

FIG. 23 depicts other alternative embodiments of a spinal implant 1660, an inserter 1680, and an intermediary piece 1670 each positioned in engagement with one another. More particularly, this figure depicts the interface between an alternative embodiment of an installation rod 1640, intermediary piece 1670, and spinal implant 1660.

Installation rod 1640 comprises a distal tip 1641 comprising a knob or increased diameter region relative to an adjacent reduced diameter region—namely, reduced diameter section 1642. Reduced diameter section 1642 may be configured so as to have a diameter that is less than a minor diameter of the threads of adjacent threaded section 1643 in some embodiments. In some embodiments, reduced diameter section 1642 may also, or alternatively, be configured so as to have a diameter that is less than a diameter of the installation rod 1640 immediately adjacent to the threaded section 1642 on the opposite side (i.e., proximal of the threaded section 1642).

In some embodiments, knob 1641 may be configured to extend all of the way through the opening in spinal implant 1660 through which installation rod 1640 extends, as shown in FIG. 23. In some embodiments, knob 1641 may comprise a flexible material such that at least a portion of knob 1641 extends beyond the perimeter of this opening after installation rod 1640 has extended through this opening. In some embodiments, one or more engagement members may be configured to be deployed within an opening 1622 that extends between upper and lower surfaces of spinal implant 1660 so as to facilitate a more secure engagement between installation rod 1640 and spinal implant 1660.

Other embodiments are contemplated in which at least a portion of installation rod 1640 may be configured to expand once it has been positioned within the opening in spinal implant 1660 through which installation rod 1640 extends. This may facilitate a friction fit between installation rod 1640 and this opening, which may negate the need for providing threads.

Adjacent to reduced diameter section 1642 is a threaded portion 1643, which is configured to be threaded with a female threaded region 1663 in spinal implant 1660. Reduced diameter section 1642 may be configured to facilitate introduction of threaded portion 1643 into female threaded region 1663 of spinal implant 1660. In certain preferred embodiments, female threaded region 1663 is spaced apart from both opposite ends of the opening through which installation rod 1640 is received. As discussed in greater detail elsewhere, this may be useful in connection with spinal implants comprised of certain materials, such as silicon nitride ceramic and other ceramic materials and/or materials with similar properties, which may be prone to fracturing at certain points during installation.

An unthreaded section 1644 is positioned adjacent and proximal to threaded portion 1643. At least a portion of unthreaded section 1644 may be configured to be tightly engaged with at least a portion of the opening through which installation rod 1640 is received. In other words, in some embodiments, unthreaded section 1644 and at least a portion of the opening through which installation rod 1640 is received that is proximal to female threaded region 1663 may have a diameter at least substantially matching the minor diameter of threaded portion 1643. In this manner, the implant and accompanying installation instrumentation may be configured such that the threaded connection between the implant and the rod is positioned internally so as to avoid unwanted forces caused by the threads. In alternative embodiments, unthreaded section 1644 may have a diameter that is slightly less than that the portion of the opening through which installation rod 1640 is received that is proximal to female threaded region 1663 so as to provide for some clearance between the installation rod 1640 and this opening along this region. However, again, preferably the threads on threaded portion 1643 and female threaded region 1663 do not extend all of the way to the proximal end of the opening through which installation rod 1640 extends.

The proximal part of the opening through which installation rod 1640 extends preferably comprises an expanded region 1665, which may further facilitate desired coupling between installation rod 1640 and spinal implant 1660 by providing clearance for the threads on threaded portion 1643. In the depicted embodiment, expanded region 1665 is defined by a frustoconical shape that tapers so as to expand the diameter of this opening towards the proximal end of the opening. However, other embodiments are contemplated. For example, in some embodiments, other shapes may be used, as long as at least a portion of the proximal portion of the opening is wider than the portion immediately adjacent to the threaded region 1663.

A second unthreaded section 1645 may be positioned adjacent to, and proximal of, unthreaded section 1644 of installation rod 1640. Second unthreaded section 1645 may comprise a larger cross-sectional diameter than unthreaded section 1644. Second unthreaded portion 1645 may be configured to engage at least primarily, if not wholly, with intermediary piece 1670, as shown in the figure. The transition between unthreaded section 1644 and second unthreaded section 1645 may comprise a taper, as illustrated in FIG. 23. Alternatively, a more abrupt transition may be formed between unthreaded section 1644 and second unthreaded section 1645.

Similarly, the main body of installation rod 1640 may have a cross-sectional diameter that is greater than second unthreaded section 1645, which main body may be configured to at least primarily, if not wholly, be engaged with inserter 1680. Likewise, the transition between second unthreaded section 1645 and the main body of installation rod 1640 may, but need not, comprise a taper.

Providing a reduced diameter region adjacent to a threaded tip, providing a threaded section within an opening configured for engagement with an installation rod such that it is spaced apart from the proximal, periphery of the opening, providing a reduced diameter section adjacent to one or more sides of a threaded section of an installation rod, and/or providing an expanded region, such as expanded region 1665, at the proximal end of such an opening may provide substantial benefits, particularly with respect to ceramic spinal implants, such as silicon nitride ceramic spinal implants and the like. Without being limited by theory, one or more of these features may ensure that the highest forces applied to threads in the spinal implant will be applied to the strongest threads and/or will only be applied to threads that are set back from the weakest part of the opening. This may substantially reduce fractures or other damage that may otherwise occur with respect to the spinal implant.

However, other embodiments are contemplated in which a threaded section need not be provided. For example, some embodiments may be configured to provide for engagement between the rod and the implant that is spaced apart from an edge and/or periphery of the implant by way of a compression or friction fit, for example, or another engagement feature that engages the rod and the implant without threads. Preferably such engagement does not apply forces, or at least applies reduced forces, to the rear portion of the hole to engage the rod. In this manner, the forces applied to the relatively weak portions of the implant may be reduced to avoid or at least reduce the chances for cracking/breaking, which, as mentioned above, may be particularly useful in connection with certain ceramic implants that may be prone to such problems.

Figure 24:
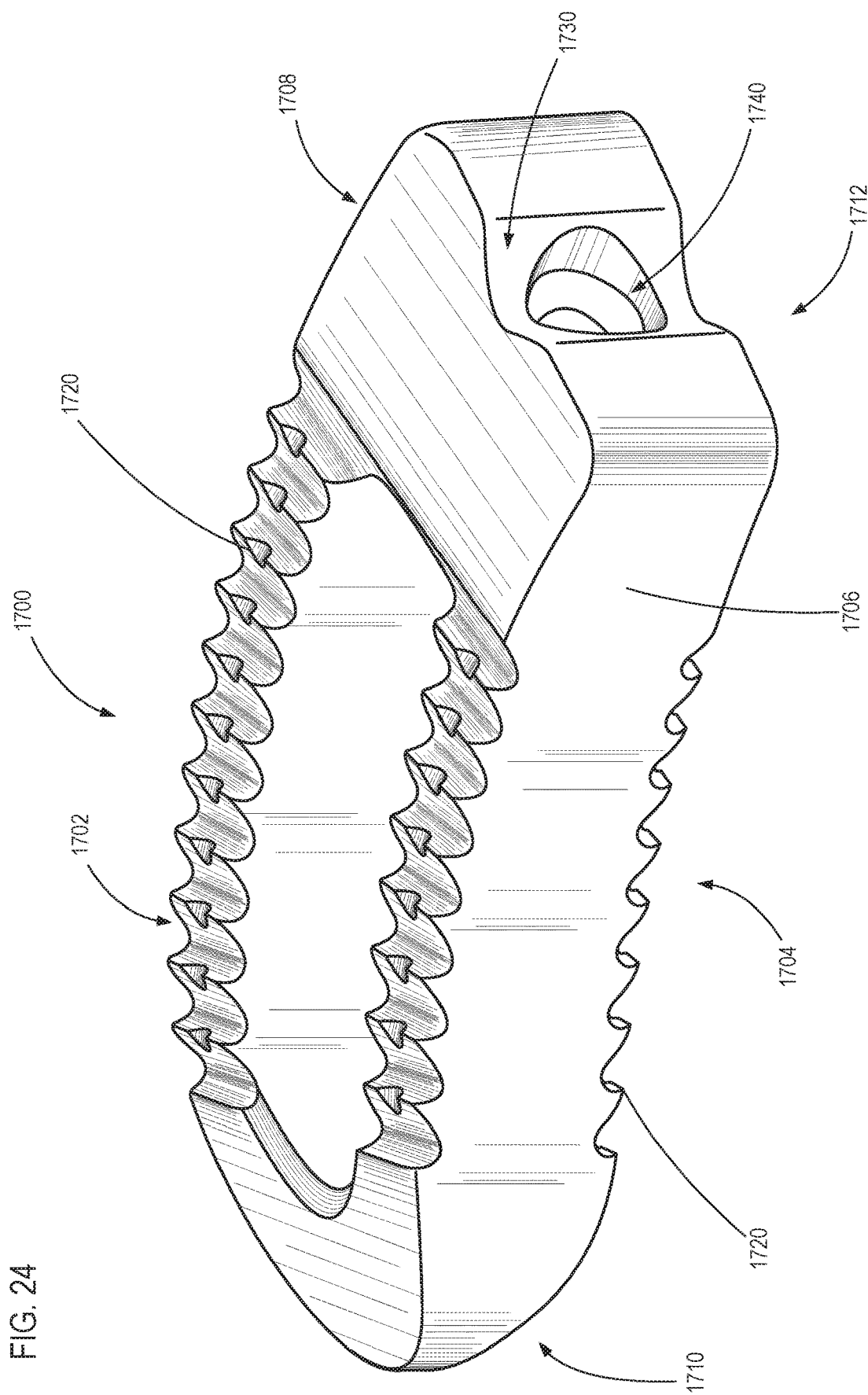
FIG. 24 is a perspective view of a spinal implant according to still another embodiment.

FIG. 24 illustrates another embodiment of a spinal implant 1700. Spinal implant 1700 comprises an upper surface 1702, a lower surface 1704, a first side wall surface 1706, a second side wall surface 1708 opposite from surface 1706, a front end wall surface 1710 comprising a nose, and a rear end wall surface 1712 opposite from front end wall surface 1710. Rear end wall surface 1712 comprises a v-shaped recess 1730. An opening 1740 is positioned within recess 1730. In the depicted embodiment, opening 1740 is positioned centrally with respect to recess 1730.

Like several of the previously-discussed embodiments, the v-shaped recess 1730 of spinal implant 1700 may be configured to directly interface with a spinal installation instrument or to indirectly couple with an intermediary piece configured to directly interface with such an instrument. However, unlike some of the previously-discussed embodiments, recess 1730 does not extend all of the way between sidewall surfaces 1706 and 1708. Instead, recess 1730 is spaced apart from both sidewall surface 1706 and sidewall surface 1708. However, recess 1730 does extend all of the way between upper surface 1702 and lower surface 1704.

Upper and lower surfaces 1702 and 1704 both comprise a plurality of teeth 1720 arranged in rows. Teeth 1720 may be configured as previously described in connection with other embodiments. Similarly, other features disclosed in connection with other embodiments may be included with spinal implant 1700, or with any other embodiment disclosed herein without such feature(s). For example, spinal implant 1700 may comprise notches, such as notches 215 in spinal implant 200, formed in one or both opposite surfaces of its nose. Similarly, spinal implant 1700 may comprise, in alternative embodiments, one or more fins, such as fins 550 as depicted on spinal implant 500.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:

1. A spinal implant, comprising:
a first sidewall;
a second sidewall opposite from the first sidewall;
an upper surface configured for engaging a first vertebra;
a lower surface configured for engaging a second vertebra adjacent to the first vertebra;
a first end wall joining the first sidewall and the second sidewall at a first end of the spinal implant;
a second end wall joining the first sidewall and the second sidewall at a second end of the spinal implant opposite from the first end, wherein the second end wall defines a second end wall surface;
a protrusion formed in the second end wall, the protrusion comprising a pair of flattened impacting surfaces including an apex therebetween; and
an opening positioned within the second end wall and encompassing at least a portion of the apex of the protrusion, wherein the opening comprises a threaded region formed within an integral portion of the spinal implant so as to be fixed relative to the second end wall, wherein the opening is defined by an external peripheral edge formed in the second end wall of the spinal implant and by an internal peripheral edge opposite from the external peripheral edge, wherein the threaded region is spaced apart from the second end wall surface, wherein the threaded region is spaced apart from the external peripheral edge and internal to the external peripheral edge, and wherein the threaded region is spaced apart from the internal peripheral edge such that the threaded region is spaced apart from both opposing ends of the opening.

2. The spinal implant of claim 1, wherein the spinal implant further comprises an expanded region within the opening.

3. The spinal implant of claim 2, wherein the expanded region comprises a diameter greater than a diameter of at least a portion of the opening adjacent to the expanded region, and wherein the expanded region is configured to provide clearance for threads on a threaded section of an installation rod.

4. The spinal implant of claim 2, wherein the expanded region is defined by a frustoconical shape that tapers so as to expand the diameter of the opening towards a proximal end of the opening.

5. The spinal implant of claim 1, wherein the spinal implant further comprises notches formed in the upper surface and the lower surface of a nose at least partially defined by the first end wall.

6. The spinal implant of claim 1, wherein the spinal implant comprises silicon nitride.

7. The spinal implant of claim 1, wherein the spinal implant comprises a ceramic material.

* * * * *